United States Patent
Horsey et al.

(10) Patent No.: US 6,599,963 B2
(45) Date of Patent: Jul. 29, 2003

(54) FLAME RETARDANT COMPOSITIONS

(75) Inventors: Douglas Wayne Horsey, Briarcliff Manor, NY (US); Stephen Mark Andrews, New Fairfield, CT (US); Leonard Harris Davis, New City, NY (US); Darrell David Dyas, Jr., Acworth, GA (US); Robert Leo Gray, Ridgefield, CT (US); Anunay Gupta, Holmdel, NJ (US); Bruce Vincent Hein, Marietta, GA (US); Joseph Stephen Puglisi, Crompound, NY (US); Ramanathan Ravichandran, Suffern, NY (US); Paul Shields, Rivervale, NJ (US); Rangarajan Srinivasan, Tarrytown, NY (US)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 69 days.

(21) Appl. No.: 09/919,973

(22) Filed: Aug. 1, 2001

(65) Prior Publication Data

US 2002/0010235 A1 Jan. 24, 2002

Related U.S. Application Data

(63) Continuation of application No. 09/714,717, filed on Nov. 16, 2000, now abandoned, which is a continuation-in-part of application No. 09/502,239, filed on Nov. 3, 1999, now Pat. No. 6,472,456, which is a continuation-in-part of application No. 09/104,718, filed on Jun. 25, 1998, now abandoned.
(60) Provisional application No. 60/051,331, filed on Jun. 30, 1997.

(51) Int. Cl.⁷ ......................... C08K 5/34; C08K 5/3495
(52) U.S. Cl. ................. 524/100; 524/101; 524/102; 524/103; 524/104; 524/105; 524/126; 524/148; 524/151
(58) Field of Search .................. 524/100, 101, 524/102, 103, 104, 105, 126, 148, 151

(56) References Cited

U.S. PATENT DOCUMENTS

| | | | |
|---|---|---|---|
| 4,173,561 A | 11/1979 | Tabana et al. | 260/45.75 |
| 4,978,699 A | 12/1990 | Kazmierczak et al. | 529/99 |
| 5,004,770 A | 4/1991 | Cortolano et al. | 524/99 |
| 5,021,486 A * | 6/1991 | Galbo | 524/100 |
| 5,025,050 A | 6/1991 | Torres | 524/91 |
| 5,077,340 A * | 12/1991 | Ravichandran et al. | |
| 5,096,950 A | 3/1992 | Galbo et al. | 524/99 |
| 5,112,890 A * | 5/1992 | Behrens et al. | 524/95 |
| 5,118,736 A | 6/1992 | Ravichandran et al. | 524/100 |
| 5,145,893 A | 9/1992 | Galbo et al. | 549/19 |
| 5,204,473 A | 4/1993 | Winter et al. | 546/188 |
| 5,300,544 A | 4/1994 | Galbo et al. | |
| 5,359,069 A | 10/1994 | Galbo et al. | 546/19 |
| 5,393,812 A | 2/1995 | Haley et al. | 524/91 |
| 5,844,026 A | 12/1998 | Galbo et al. | 524/100 |

FOREIGN PATENT DOCUMENTS

| | | |
|---|---|---|
| EP | 0366057 | 5/1990 |
| EP | 0792911 | 9/1997 |
| WO | 90/06691 | 6/1990 |

* cited by examiner

Primary Examiner—Kriellion A. Sanders
(74) Attorney, Agent, or Firm—Tyler A. Stevenson

(57) ABSTRACT

Hindered amine compounds containing a group of the formula

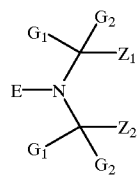

where $G_1$ and $G_2$ are independently alkyl of 1 to 4 carbon atoms or are together pentamethylene, $Z_1$ and $Z_2$ are each methyl, or $Z_1$ and $Z_2$ together form a linking moiety which may additionally be substituted by an ester, ether, amide, amino, carboxy or urethane group, and E is alkoxy, cycloalkoxy, aralkoxy, aryloxy, —O—CO—$OZ_3$, —O—Si$(Z_4)_3$, —O—PO$(OZ_5)_2$ or —O—$CH_2$—$OZ_6$ where $Z_3$, $Z_4$, $Z_5$ and $Z_6$ are selected from the group consisting of hydrogen, an aliphatic, araliphatic and aromatic moiety, when added to a wide variety of polymeric substrates, particularly polyolefins and styrenic polymers, surprisingly bestow flame retardant properties to such compositions. Polyolefins, especially polypropylene, can be made flame retardant by the incorporation therein of a synergistic mixture of a selected hindered amine substituted by an alkoxy, cycloalkoxy or hydroxyalkoxy moiety and a selected organic or inorganic brominated and/or phosphorus containing flame retardant, such as ammonium polyphosphate or decabromodiphenyl oxide wherein the amount of organic or inorganic flame retardant required to achieve an acceptable level of flame retardancy is significantly reduced compared to that needed when the hindered amine is not present.

17 Claims, No Drawings

FLAME RETARDANT COMPOSITIONS

This application claims the benefit under 35 USC 119(e) of U.S. Provisional Application Serial No. 60/051,331, filed on Jun. 30, 1997; and is a continuation of application Ser. No. 09/714,717, filed Nov. 16, 2000, now abandoned which is a continuation-in-part of application Ser. No. 09/502,239, filed Nov. 3, 1999 now U.S. Pat. No. 6,472,456 which is a continuation-in-part of application Ser. No. 09/104,718, filed on Jun. 25, 1998 now abandoned.

The instant invention pertains to a method of flame retarding a polymeric substrate by adding thereto an effective flame retarding amount of a selected hindered amine compound.

The instant invention also pertains to a method of flame retarding a polymeric substrate by adding thereto an effective flame retarding amount of a synergistic mixture of a selected hindered amine compound and an organic or inorganic flame retardant which contains bromine and/or phosphorus moieties.

BACKGROUND OF THE INVENTION

The hindered amines have long been recognized as light and/or as thermal stabilizers for a host of organic materials subject to degradation induced by oxygen, heat or actinic light. The patent and academic publication literature is replete with references to these hindered amine compounds and their valuable stabilizing efficacies. There is no mention or suggestion in any of such references that the hindered amines themselves are also flame retardants per se.

Particularly relevant are U.S. Pat. Nos. 5,004,770; 5,096,950; 5,204,473; 5,300,544 and 5,844,026 as well as applications Ser. Nos. 09/257,711 and 09/253,161. These references pertain to various N-hydrocarbyloxy substituted hindered amines (so called NOR and NOROL hindered amines) and to various compositions stabilized therewith. As mentioned above, none of these reference disclose or even hint that the compositions stabilized with the NOR or NOROL hindered amines alone are flame retardant. This inherent property was never discovered, not even serendipitously, until the present invention was made. That this is so, is in itself evidence that even those of considerable skill in the hindered amine stabilizer art were quite surprised by this unexpected discovery. The fact that a large amount of an inorganic or organic classical bromine and/or phosphorus containing flame retardant could be substituted by a small amount of a NOR or NOROL hindered amine and still achieve very acceptable flame retardancy was also quite unexpected. This is highly beneficial for the environment and for safety reasons. Accordingly, polymeric substrate compositions made flame retardant by incorporating therein a synergistic mixture of a NOR or NOROL hindered amine plus a classic inorganic or organic bromine and/or phosphorus containing flame retardant is also quite surprising, unexpected and clearly not obvious to those of skill in this stabilizer art. This invention affords the public a valuable method for flame retarding polymers which cannot be gleaned from any of the prior art references.

U.S. Pat. No. 5,393,812 does describe polyolefin compositions which are made flame retardant by a combination of a halogenated hydrocarbyl phosphate or phosphonate ester flame retardant in combination with a alkoxyamine functional hindered amine, but there is no suggestion that the hindered amine itself is responsible for the flame retardancy, but rather that the hindered amine is preventing delustering and other undesirable effects from occurring in these polyolefin compositions.

European Application No. 0 792 911 A2, published after the filing date of the parent provisional application Serial No. 60/051,331, discloses that alkoxyamine functional hindered amines may have some flame retarding properties, but are quite effective when used to enhance the flame retarding efficacy of tris(trihalogenopentyl) phosphate flame retardants. This publication is somewhat ambivalent as to whether the alkoxyamine functional hindered amine are really themselves flame retardants in the absence of the recognized phosphate flame retardant.

The flame retardant (FR) market today is comprised of products which function to interfere with the combustion process by chemical and/or physical means. Mechanistically these FRs have been proposed to function during combustion of an article in either the gas phase, the condensed phase or both. The organohalogens are proposed to generate halogen species (e.g. HX) which interferes in the gas phase with free radical organic "fuel" from the polymer substrate. Synergists are proposed to react with HX to form additional chemical species with interfere with combustion in the gas phase, such as reaction of antimony oxide with HX to form antimony halide and water vapor. Still other flame retardant classes are proposed to impart efficacy in the "condensed" phase such as forming a protective char layer on the polyester, or forming an intumescent or foaming on the polymer surface. The char or intumescent layer is thought either to prevent organic fuel from migrating from the polymer into the vapor phase where it can fuel combustion, or the char can act as a thermal shield to protect the underlying polymer article from thermally induced decomposition and generation of fuel. Phosphorus compound of various classes (e.g. halo- or non-halogenated) are an example. Further still, other classes of compounds are proposed to function in the condensed and/or vapor phase. Metal hydrates or metal oxides are proposed to generate water vapor under thermal conditions, the water acting to dilute the fuel mix in the combustion zone and to remove heat from the flame zone via conversion of water to vapor. Alumina trihydrate, magnesium hydroxide or oxide, and other compounds are reported to function in this way.

These state of the art chemistries described above have various detrimental aspects in addition to the effective flame retarding attributes mentioned. Certain organobrominated compounds are under governmental scrutiny for the generation of toxic by-products during the production or combustion such as dioxanes from polybrominated diphenyl oxides. Certain metal-containing flame retardants, notably antimony oxides, are under scrutiny for worker exposure and toxicity reasons. Antimony oxides often contain trace amounts of arsenic compounds which are suspected cancinogens. Overall, a growing concern has arisen regarding the generation of smoke and toxic gases which are evolved from these flame retardants during a fire. While the classic FRs may be effective combustion suppressants, the toxic gases they form pose a threat to human exposure.

The instant invention alleviates some of the detrimental aspects of the current state of the art which the use of large amounts of commercial flame retardants pose. The instant NOR or NOROL hindered amines are non-halogenated and free of heavy metals, thus avoiding generation of corrosive HX gases and avoiding exposure to toxic metals. In some applications, the instant invention provides a direct replacement for current FR systems where the instant NOR or NOROL hindered amine compounds provide a complimentary enhancement or synergistic system for heavy metals (e.g. antimony oxide replacement in ABS) where good flame retardancy can be achieved by using less classic FR agent in the presence of the instant NOR or NOROL hindered amine compound.

DETAILED DISCLOSURE

The instant invention pertains to a method of flame retarding a polymeric substrate by adding thereto an effective flame retarding amount of a hindered amine compound containing a group of the formula

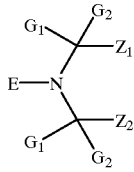

where $G_1$ and $G_2$ are independently alkyl of 1 to 4 carbon atoms or are together pentamethylene, $Z_1$ and $Z_2$ are each methyl, or $Z_1$ and $Z_2$ together form a linking moiety which may additionally be substituted by an ester, ether, amide, amino, carboxy or urethane group, and E is alkoxy, cycloalkoxy, aralkoxy, aryloxy, —O—CO—$OZ_3$, —O—Si$(Z_4)_3$, —O—PO$(OZ_5)_2$ or —O—CH$_2$—$OZ_6$ where $Z_3$, $Z_4$, $Z_5$ and $Z_6$ are selected from the group consisting of hydrogen, an aliphatic, araliphatic and aromatic moiety.

Preferably E is alkoxy, cycloalkoxy or aralkoxy. Most preferably E is methoxy, propoxy, cyclohexyloxy or octyloxy.

More particularly, the instant invention relates a method of flame retarding a polymeric substrate which comprises adding to said substrate an effective flame retarding amount of a hindered amine of a hindered amine compound having a formula of structure A—R

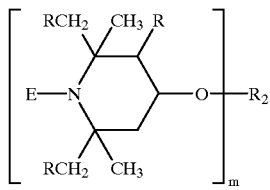
(A)

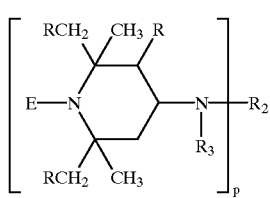
(B)

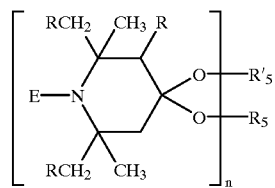
(C)

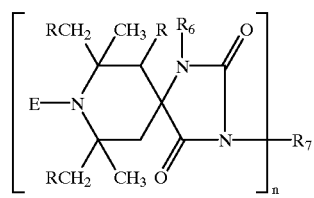
(D)

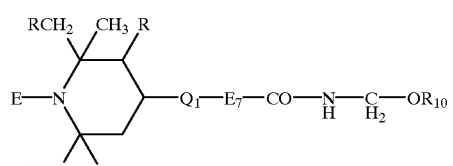
(E)

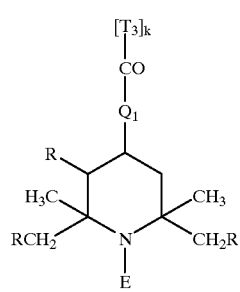
(F)

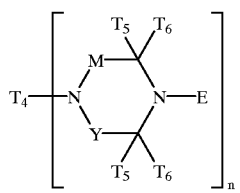
(G)

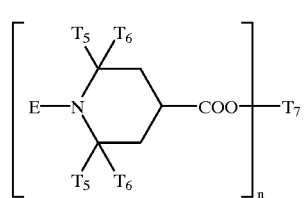
(H)

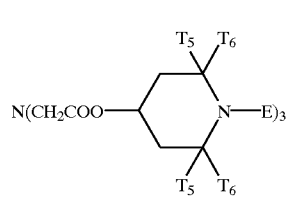
(I)

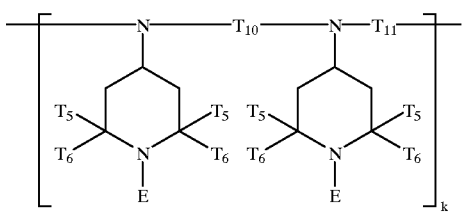 (J)

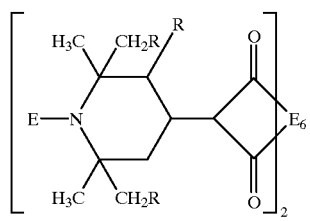 (P)

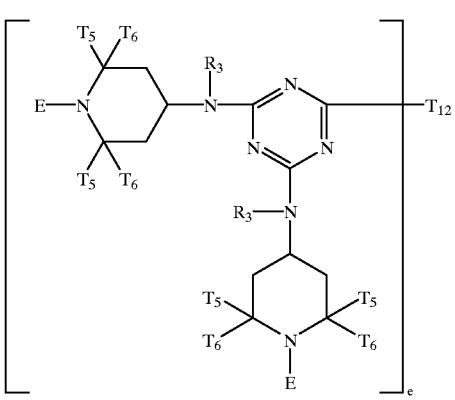 (K)

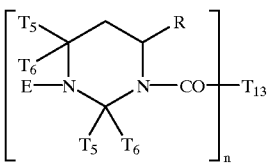 (Q)

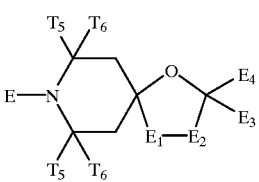 (R)

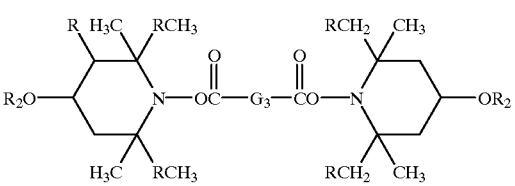 (L)

wherein
E is alkoxy of 1 to 18 carbon atoms, cycloalkoxy of 5 to 12 carbon atoms or aralkoxy of 7 to 15 carbon atoms,
R is hydrogen or methyl,
m is 1 to 4,
when m is 1,
$R_2$ is hydrogen, $C_1$–$C_{18}$alkyl or said alkyl optionally interrupted by one or more oxygen atoms, $C_2$–$C_{12}$alkenyl, $C_6$–$C_{10}$aryl, $C_7$–$C_{18}$aralkyl, glycidyl, a monovalent acyl radical of an aliphatic, cycloaliphatic or aromatic carboxylic acid, or a carbamic acid, preferably an acyl radical of an aliphatic carboxylic acid having 2–18C atoms, of a cycloaliphatic carboxylic acid having 5–12 C atoms or of an aromatic carboxylic acid having 7–15 C atoms, or

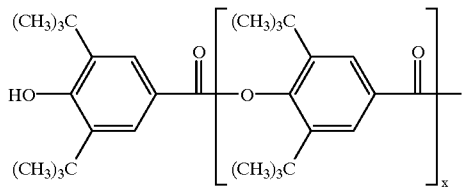 (M)

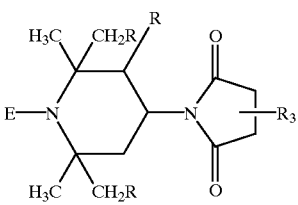 (N)

wherein x is 0 or 1,

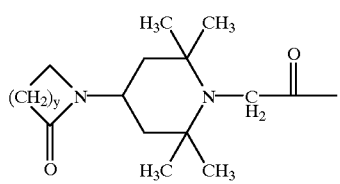 (O)

wherein y is 2–4;
when m is 2,
$R_2$ is $C_1$–$C_{12}$alkylene, $C_1$–$C_{12}$alkenylene, xylylene, a divalent acyl radical of an aliphatic, cycloaliphatic, araliphatic or aromatic dicarboxylic acid or of a dicarbamic acid, preferably an acyl radical of an aliphatic dicarboxylic acid having 2–18 C atoms, of a cycloaliphatic or aromatic dicarboxylic acid having 8–14 C atoms, or of an aliphatic, cycloaliphatic or aromatic dicarbamic acid having 8–14 C atoms;

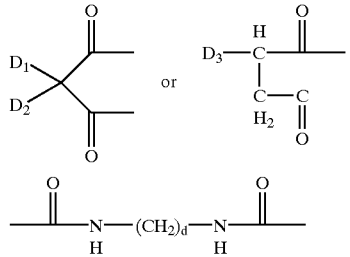

wherein $D_1$ and $D_2$ are independently hydrogen, an alkyl radical containing up to 8 carbon atoms, an aryl or aralkyl radical including 3,5-di-t-butyl4-hydroxybenzyl radical, $D_3$ is hydrogen, or an alkyl or alkenyl radical containing up to 18 carbon atoms, and d is 0–20;
when m is 3, $R_2$ is a trivalent acyl radical of an aliphatic, unsaturated aliphatic, cycloaliphatic, or aromatic tricarboxylic acid;
when m is 4, $R_2$ is a tetravalent acyl radical of a saturated or unsaturated aliphatic or aromatic tetracarboxylic acid including 1,2,3,4-butanetetracarboxylic acid, 1,2,3,4-but-2-ene-tetracarboxylic, and 1,2,3,5- and 1,2,4,5-pentanetetracarboxylic acid;
p is 1, 2 or 3,
$R_3$ is hydrogen, $C_1$–$C_{12}$alkyl, $C_5$–$C_7$cycloalkyl, $C_7$–$C_9$aralkyl, $C_2$–$C_{18}$alkanoyl, $C_3$–$C_5$alkenoyl or benzoyl;
when p is 1,
$R_4$ is hydrogen, $C_1$–$C_{18}$alkyl, $C_5$–$C_7$cycloalkyl, $C_2$–$C_8$alkenyl, unsubstituted or subs by a cyano, carbonyl or carbamide group, aryl, aralkyl, or it is glycidyl, a group of the formula —CH$_2$—CH(OH)—Z or of the formula —CO—Z or —CONH—Z wherein Z is hydrogen, methyl or phenyl; or a group of the formulae

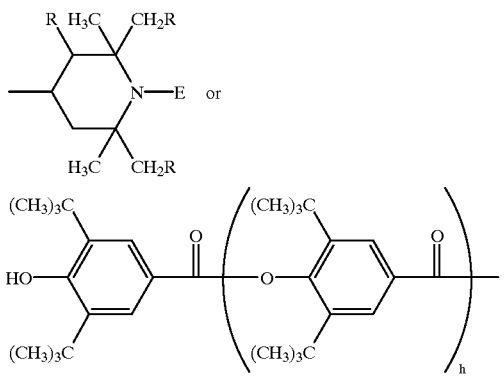

where h is 0 or 1,
$R_3$ and $R_4$ together, when p is 1, can be alkylene of 4 to 6 carbon atoms or 2-oxo-polyalkylene the cyclic acyl radical of an aliphatic or aromatic 1,2- or 1,3-dicarboxylic acid,
when p is 2, $R_4$ is a direct bond or is $C_1$–$C_{12}$alkylene, $C_6$–$C_{12}$arylene, xylylene, a —CH$_2$CH(OH)—CH$_2$ group or a group —CH$_2$—CH(OH)—CH$_2$—O—X—O—CH$_2$—CH(OH)—CH$_2$— wherein X is $C_2$–$C_{10}$alkylene, $C_6$–$C_{15}$arylene or $C_6$–$C_{12}$cycloalkylene; or, provided that $R_3$ is not alkanoyl, alkenoyl or benzoyl, $R_4$ can also be a divalent acyl radical of an aliphatic, cycloaliphatic or aromatic dicarboxylic acid or dicarbamic acid, or can be the group —CO—; or
$R_4$ is

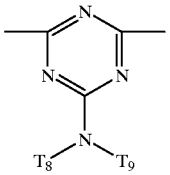

where $T_8$ and $T_9$ are independently hydrogen, alkyl of 1 to 18 carbon atoms, or $T_8$ and $T_9$ together are alkylene of 4 to 6 carbon atoms or 3-oxapentamethylene, preferably $T_8$ and $T_9$ together are 3-oxapentamethylene;
when p is 3,
$R_4$ is 2,4,6-triazinyl,
n is 1 or 2,
when n is 1,
$R_5$ and $R'_5$ are independently $C_1$–$C_{12}$ alkyl, $C_2$–$C_{12}$ alkenyl, $C_7$C$_{12}$ aralkyl, or $R_5$ is also hydrogen, or $R_5$ and $R'_5$ together are $C_2$–$C_8$alkylene or hydroxyalkylene or $C_4$–$C_{22}$acyloxyalkylene;
when n is 2,
$R_5$ and $R'_5$ together are (—CH$_2$)$_2$C(CH$_2$—)$_2$;
$R_6$ is hydrogen, $C_1$–$C_{12}$alkyl, allyl, benzyl, glycidyl or $C_2$–$C_6$alkoxyalkyl;
when n is 1,
$R_7$ is hydrogen, $C_1$–$C_{12}$alkyl, $C_3$–$C_5$alkenyl, $C_7$–$C_9$aralkyl, $C_5$–$C_7$cycloalkyl, $C_2$–$C_4$hydroxyalkyl, $C_2$–$C_6$alkoxyalkyl, $C_{6-10}$ aryl, glycidyl, a group of the formula —(CH$_2$)$_t$—COO—Q or of the formula —(CH$_2$)$_t$—O—CO—Q wherein t is 1 or 2, and Q is $C_1$–$C_4$alkyl or phenyl; or
when n is 2,
$R_7$ is $C_2$–$C_{12}$alkylene, $C_6$–$C_{12}$arylene, a group —CH$_2$CH(OH)—CH$_2$O—X—O—CH$_2$—CH(OH)—CH$_2$— wherein X is $C_2$–$C_{10}$alkylene, $C_6$–$C_{15}$arylene or $C_6$–$C_{12}$cycloalkylene, or a group —CH$_2$CH(OZ')CH$_2$—(OCH$_2$—CH(OZ')CH$_2$)$_2$— wherein Z' is hydrogen, $C_1$–$C_{18}$alkyl, allyl, benzyl, $C_2$–$C_{12}$alkanoyl or benzoyl;
$Q_1$ is —N(R$_8$)— or —O—; $E_7$ is $C_1$–$C_3$ alkylene, the group —CH$_2$—CH(R$_9$)—O— wherein $R_9$ is hydrogen, methyl or phenyl, the group —(CH$_2$)$_3$—NH— or a direct bond;
$R_{10}$ is hydrogen or $C_1$–$C_{18}$ alkyl, $R_8$ is hydrogen, $C_1$–$C_{18}$alkyl, $C_5$–$C_7$cycloalkyl, $C_7$–$C_{12}$aralkyl, cyanoethyl, $C_6$–$C_{10}$aryl, the group —CH$_2$—CH(R$_9$)—OH wherein $R_9$ has the meaning defined above; a group of the formula

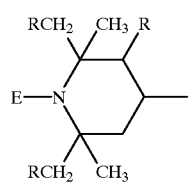

or a group of the formula

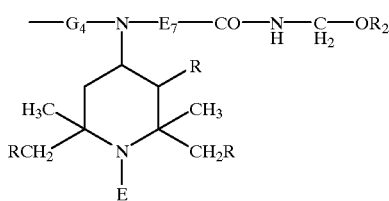

wherein $G_4$ is $C_2$–$C_{12}$alkylene or $C_6$–$C_{12}$arylene; or $R_8$ is a group —$E_7$—CO—NH—CH$_2$—OR$_{10}$;

Formula F denotes a recurring structural unit of a polymer where $T_3$ is ethylene or 1,2-propylene, is the repeating structural unit derived from an alpha-olefin copolymer with an alkyl acrylate or methacrylate; preferably a copolymer of ethylene and ethyl acrylate, and where k is 2 to 100;

$T_4$ has the same meaning as $R_4$ when p is 1 or 2, $T_5$ is methyl, $T_6$ is methyl or ethyl, or $T_5$ and $T_6$ together are tetramethylene or pentamethylene, preferably $T_5$ and $T_6$ are each methyl, M and Y are independently methylene or carbonyl, and $T_4$ is ethylene where n is 2;

$T_7$ is the same as $R_7$, and $T_7$ is preferably octamethylene where n is 2, $T_{10}$ and $T_{11}$ are independently alkylene of 2 to 12 carbon atoms, or $T_{11}$ is

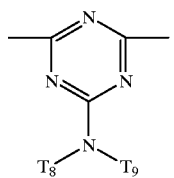

$T_{12}$ is piperazinyl,

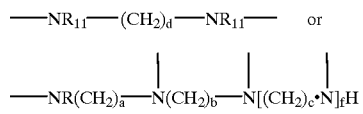

where $R_{11}$ is the same as $R_3$ or is also

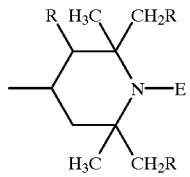

a, b and c are independently 2 or 3, and f is 0 or 1, preferably a and c are each 3, b is 2 and f is 1; and e is 2, 3 or 4, preferably 4;

$T_{13}$ is the same as $R_2$ with the proviso that $T_{13}$ cannot be hydrogen when n is 1;

$E_1$ and $E_2$, being different, each are —CO— or —N($E_5$)— where $E_5$ is hydrogen, $C_1$–$C_{12}$ alkyl or $C_4$–$C_{22}$ alkoxycarbonylalkyl, preferably $E_1$ is —CO— and $E_2$ is —N($E_5$)—, $E_3$ is hydrogen, alkyl of 1 to 30 carbon atoms, phenyl, naphthyl, said phenyl or said naphthyl substituted by chlorine or by alkyl of 1 to 4 carbon atoms, or phenylalkyl of 7 to 12 carbon atoms, or said phenylalkyl substituted by alkyl of 1 to 4 carbon atoms, $E_4$ is hydrogen, alkyl of 1 to 30 carbon atoms, phenyl, naphthyl or phenylalkyl of 7 to 12 carbon atoms, or $E_3$ and $E_4$ together are polymethylene of 4 to 17 carbon atoms, or said polymethylene substituted by up to four alkyl groups of 1 to 4 carbon atoms, preferably methyl, $E_6$ is an aliphatic or aromatic tetravalent radical, $R_2$ of formula (N) is a previously defined when m is 1;

$G_1$ a direct bond, $C_1$–$C_{12}$ alkylene, phenylene or —NH—G'—NH wherein G' is $C_1$–$C_{12}$ alkylene; or wherein the hindered amine compound is a compound of the formula I, II, III, IV, V, VI, VII, VIII, IX, X or XI

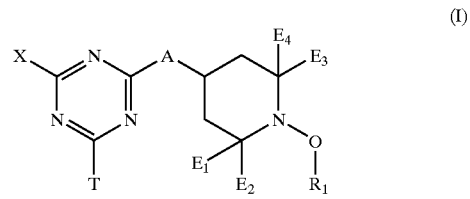

(I)

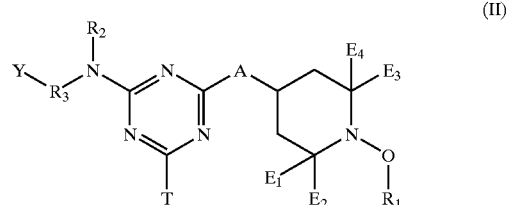

(II)

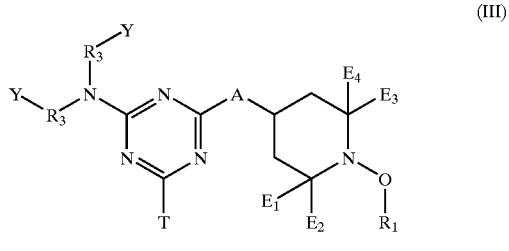

(III)

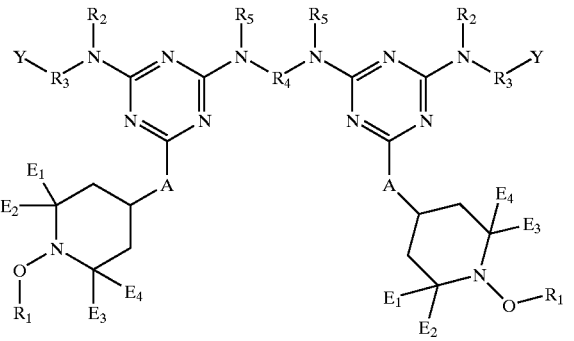

(IV)

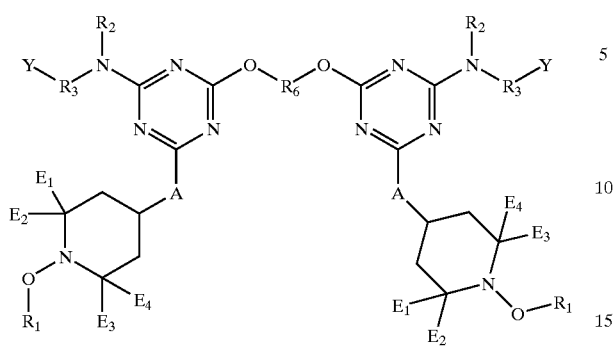

(V)

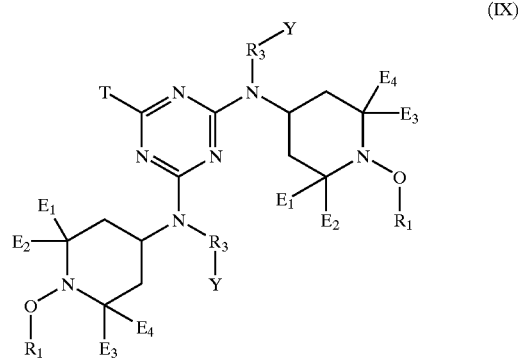

(IX)

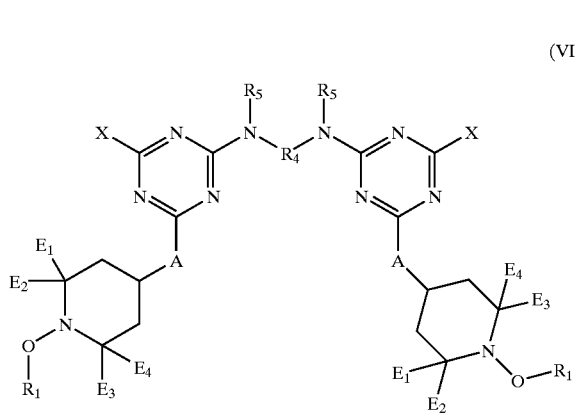

(VI)

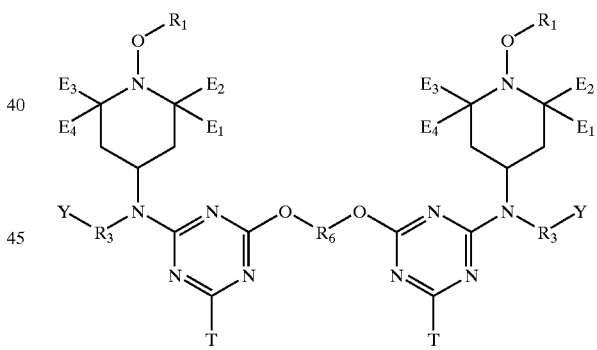

(X)

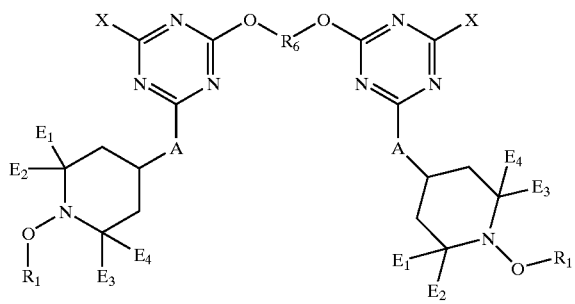

(VII)

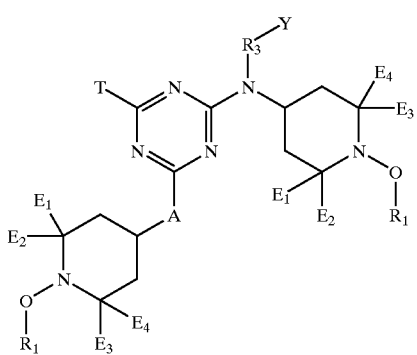

(VIII)

wherein $E_1$, $E_2$, $E_3$ and $E_4$ are independently alkyl of 1 to 4 carbon atoms, or $E_1$ and $E_2$ are independently alkyl of 1 to 4 carbon atoms and $E_3$ and $E_4$ taken together are pentamethylene, or $E_1$ and $E_2$; and $E_3$ and $E_4$ each taken together are pentamethylene, $R_1$ is alkyl of 1 to 18 carbon atoms, cycloalkyl of 5 to 12 carbon atoms, a bicyclic or tricyclic hydrocarbon radical of 7 to 12 carbon atoms, phenylalkyl of 7 to 15 carbon atoms, aryl of 6 to 10 carbon atoms or said aryl substituted by one to three alkyl of 1 to 8 carbon atoms, $R_2$ is hydrogen or a linear or branched chain alkyl of 1 to 12 carbon atoms, $R_3$ is alkylene of 1 to 8 carbon atoms, or $R_3$ is —CO—, —CO—$R_4$—, —CONR$_2$—, or —CO—NR$_2$—R$_4$—, $R_4$ is alkylene of 1 to 8 carbon atoms, $R_5$ is hydrogen, a linear or branched chain alkyl of 1 to 12 carbon atoms, or

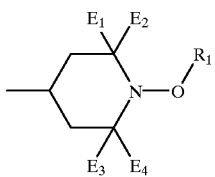

or when $R_4$ is ethylene, two $R_5$ methyl substituents can be linked by a direct bond so that the triazine bridging group —N($R_5$)—$R_4$—N($R_5$)— is a piperazin-1,4-diyl moiety, $R_6$ is alkylene of 2 to 8 carbon atoms or $R_6$ is

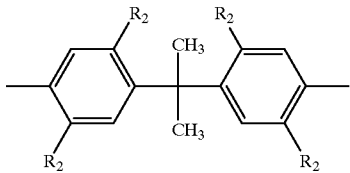

with the proviso that Y is not —OH when $R_6$ is the structure depicted above,

A is —O— or —N$R_7$— where $R_7$ is hydrogen, a straight or branched chain alkyl of 1 to 12 carbon atoms, or $R_7$ is

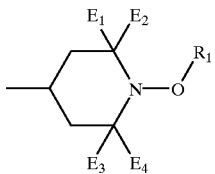

T is phenoxy, phenoxy substituted by one or two alkyl groups of 1 to 4 carbon atoms, alkoxy of 1 to 8 carbon atoms or —N($R_2$)$_2$ with the stipulation that $R_2$ is not hydrogen, or T is

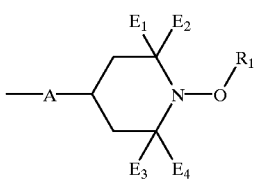

X is —NH$_2$, —NCO, —OH, —O-glycidyl, or —NHNH$_2$, and

Y is —OH, —NH$_2$, —NHR$_2$ where R$_2$ is not hydrogen; or Y is —NCO, —COOH, oxiranyl, —O—glycidyl, or —Si(OR$_2$)$_3$; or the combination R$_3$—Y— is —CH$_2$CH(OH)R$_2$ where R$_2$ is alkyl or said alkyl interrupted by one to four oxygen atoms, or R$_3$—Y— is —CH$_2$OR$_2$; or wherein the hindered amine compound is a mixture of N,N',N'''-tris{2,4-bis[(1-hydrocarbyloxy-2,2,6,6-tetramethylpiperidin-4yl)alkylamino]-s-triazin-6-yl}-3,3'-ethylenediiminodipropylamine; N,N',N'''-tris{2,4-bis[(1-hydrocarbyloxy-2,2,6,6-tetramethylpiperidin-4yl)alkylamino]-s-triazin-6-yl}-3,3'-ethylenediiminodipropylamine, and bridged derivatives as described by formulas I, II, IIA and III $R_1NH$—$CH_2CH_2CH_2NR_2CH_2CH_2NR_3CH_2CH_2CH_2NHR_4$ (I)

T—$E_1$—T, (II)

T—E, (IIA)

G—$E_1$—$G_1$—$E_1$—$G_2$ (III)

where in the tetraamine of formula I
$R_1$ and $R_2$ are the s-triazine moiety E; and one of $R_3$ and $R_4$ is the s-triazine moiety E with the other of $R_3$ or $R_4$ being hydrogen, E is

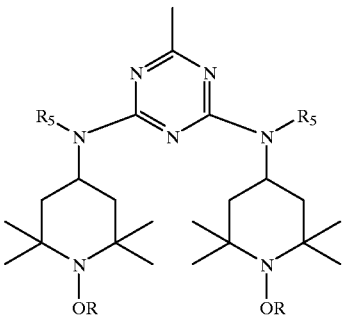

R is methyl, propyl, cyclohexyl or octyl, preferably cyclohexyl, $R_5$ is alkyl of 1 to 12 carbon atoms, preferably n-butyl, where in the compound of formula II or IIA when R is propyl, cyclohexyl or octyl, T and $T_1$ are each a tetraamine substituted by $R_1$–$R_4$ as is defined for formula I, where (1) one of the s-triazine moieties E in each tetraamine is replaced by the group $E_1$ which forms a bridge between two tetraamines T and $T_1$, $E_1$ is

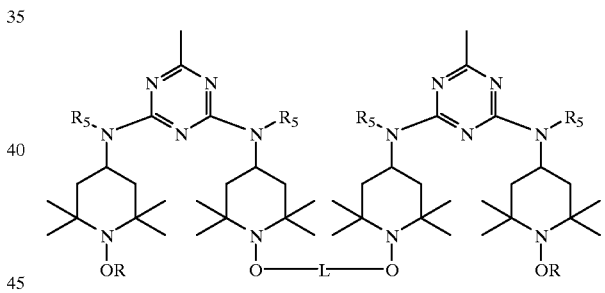

or (2) the group $E_1$ can have both termini in the same tetraamine T as in formula IIA where two of the E moieties of the tetraamine are replaced by one $E_1$ group, or (3) all three s-triazine substituents of tetraamine T can be $E_1$ such that one $E_1$ links T and $T_1$ and a second $E_1$ has both termini in tetraamine T, L is propanediyl, cyclohexanediyl or octanediyl;

where in the compound of formula III

G, $G_1$ and $G_2$ are each tetraamines substituted by $R_1$–$R_4$ as defined for formula I, except that G and $G_2$ each have one of the s-triazine moieties E replaced by $E_1$, and $G_1$ has two of the triazine moieties E replaced by $E_1$, so that there is a bridge between G and $G_1$ and a second bridge between $G_1$ and $G_2$;

which mixture is prepared by reacting two to four equivalents of 2,4-bis[(1-hydrocarbyloxy-2,2,6,6-piperidin4-yl)butylamino]-6-chloro-s-triazine with one equivalent of N,N'-bis(3-aminopropyl)ethylenediamine.

In the structures A to R, if any substituents are $C_1$–$C_{18}$ alkyl, they are for example methyl, ethyl, n-propyl, n-butyl, sec-butyl, tert-butyl, n-hexyl, n-octyl, 2-ethylhexyl, n-nonyl, n-decyl, n-undecyl, n-dodecyl, n-tridecyl, n-tetradecyl, n-hexadecyl or n-octadecyl. Typical cycloalkyl groups include cyclopentyl and cyclohexyl; typical cycloalkenyl groups include cyclohexenyl; while typical aralkyl groups include benzyl, alpha-methyl-benzyl, alpha, alpha-dimethylbenzyl or phenethyl. $C_1$–$C_{12}$ alkyl and cyclohexyl are preferred.

If $R_2$ is a monovalent acyl radical of a carboxylic acid, it is for example an acyl radical of acetic acid, stearic acid, salicyclic acid, benzoic acid or β-(3,5-di-tert-butyl-4-hydroxyphenyl) propionic acid.

If $R_2$ is a divalent acyl radical of a dicarboxylic acid, it is for example an acyl radical of oxalic acid, adipic acid, succinic acid, suberic acid, sebacic acid, phthalic acid dibutylmalonic acid, dibenzylmalonic acid or butyl-(3,5-di-tert-butyl4-hydropxybenzyl)-malonic acid, or bicycloheptenedicarboxylic acid, with succinates, sebacates, phthalates and isophthalates being preferred.

If $R_2$ is a divalent acyl radical of a dicarbamic acid, it is for example an acyl radical of hexamethylenedicarbamic acid or of 2,4-toluylenedicarbamic acid.

The instant NOR hindered amine compounds as described above are known in the prior art and are prepared as taught in U.S. Pat. Nos. 5,004,770; 5,096,950; 5,204,473 and 5,300,544 and in Ser. No. 08/885,613.

These references claim compositions where the effective stabilizing amount of the NOR-hindered amine is up to 5% by weight based on the polymeric substrate. Inasmuch as the amount of NOR compound in the instant invention can be up to 10% by weight of the polymer substrate, the instant invention also pertains to flame retardant compositions which comprise (a) a polymer, and
(b) 5.1 to 10% (preferably 5.1 to 8%) by weight of a NOR hindered amine as described supra based on the weight of said polymer.

While the polymeric substrate can be any of a wide variety of polymeric types including polyolefins, polystyrenics, and PVC, but preferably the polymer substrate is selected from the group of resins consisting of the polyolefins, the thermoplastic olefins, styrenic polymers and copolymers, ABS and polymers which contain hetero atoms double bonds or aromatic rings. Especially preferred are polypropylene, polyethylene, thermoplastic olefin (TPO), ABS and high impact polystyrene.

The effective flame retarding amount of the hindered amine is that needed to show flame retarding efficacy as measured by one of the standard methods used to assess flame retardancy. These include the NFPA 701 Standard Methods of Fire Tests for Flame-Resistant Textiles and Films, 1989 and 1996 editions; the UL 94 Test for Flammability of Plastic Materials for Parts in Devices and Appliances, 5th Edition, Oct. 29, 1996; Limiting Oxygen Index (LOI), ASTM D-2863; and Cone Calorimetry, ASTM E-1354.

The effective amount of hindered amine needed to achieve flame retardancy is from 0.25 to 10% by weight based on the polymeric substrate; preferably 0.5 to 8% by weight; and most preferably 0.5 to 2% by weight.

While the instant NOR-hindered amines in general possess this desirable flame retarding efficacy, the preferred hindered amines are those where E is alkoxy, cycloalkoxy or aralkoxy; most preferably where E is methoxy, propoxy, octyloxy or cyclohexyloxy, especially cyclohexyloxy. It is surprising that the NOR-hindered amines possess this flame retarding activity.

More particularly, the flame retardant compounds useful in the instant invention are preferably selected from the group consisting of tetraphenyl resorcinol diphosphite (FYROLFLEX® RDP, Akzo Nobel), chloroalkyl phosphate esters (ANTIBLAZE® AB-100, Albright & Wilson; FYROL® FR-2, Akzo Nobel)

polybrominated diphenyl oxide (DE-60F, Great Lakes Corp.)

decabromodiphenyl oxide (DBDPO; SAYTEX® 102E)

antimony trioxide ($Sb_2O_3$), antimony pentoxide ($Sb_2O_5$), tris[3-bromo-2,2-(bromomethyl)propyl]phosphate (PB 370®, FMC Corp.), triphenyl phosphate, bis(2,3-dibromopropyl ether) of bisphenol A (PE68), ammonium polyphosphate (APP) or (HOSTAFLAM® AP750), resorcinol diphosphate oligomer (RDP), brominated epoxy resin, ethylene-bis(tetrabromophthalimide) (BT93), bis(hexachlorocyclopentadieno)cyclooctane (DECLORANE PLUS®), calcium sulfate chlorinated paraffins, magnesium carbonate, melamine phosphates, melamine pyrophosphates, molybdenum trioxide, zinc oxide, 1,2-bis(tribromophenoxy)ethane (FF680), tetrabromo-bisphenol A (SAYTEX® RB100), magnesium hydroxide, alumina trihydrate, zinc borate, ethylenediamine diphosphate (EDAP)

silica, silicones, calcium silicate, and magnesium silicate.

Coadditives found useful for use with the instant NOR-hindered amine compounds in flame retardant compositions are as follows:

Phosphorus Compounds tris(2,4-di-tert-butylphenyl) phosphite, (IRGAFOS® 168, Ciba Specialty Chemicals Corp.);

bis(2,4-di-tert-butyl-6-methylphenyl) ethyl phosphite, (IRGAFOS® 38, Ciba Specialty Chemicals Corp.);

2,2',2"-nitrilo[triethyl-tris-(3,3',5,5'-tetra-tert-butyl-1,1'-biphenyl-2,2'-diyl)phosphite], (IRGAFOS® 12, Ciba Specialty Chemicals Corp.);

tetrakis(2,4-di-butylphenyl) 4,4'-biphenylenediphosphonite, (IRGAFOS® P-EPQ, Ciba Specialty Chemicals Corp.);

tris(nonylphenyl) phosphite, (TNPP®, General Electric);

bis(2,4-di-tert-butylphenyl) pentaerythrityl diphosphite, (ULTRANOX® 626, General Electric);

2,2'-ethylidenebis(2,4-di-tert-butylphenyl) fluorophosphite, (ETHANOX® 398, Ethyl Corp.)

2-butyl-2-ethylpropan-1,3-diyl 2,4,6-tri-tert-butylphenyl phosphite, (ULTRANOX® 641, General Electric).

Flame Retardants tris[3-bromo-2,2-bis(bromomethyl)propyl]phosphate, (PB 370®, FMC Corp.)
decabromodiphenyl oxide, (DBDPO);
ethylene bis-(tetrabromophthalimide), (SAYTEX® BT-93);
ethylene bis-(dibromo-norbornanedicarboximide), (SAYTEX® BN-451)

UV Absorbers 2-(2-hydroxy-3,5-di-α-cumylphenyl)-2H-benzotriazole, (TINUVIN® 234, Ciba Specialty Chemicals Corp.);
2-(2-hydroxy-5-methylphenyl)-2H-benzotriazole, (TINUVIN® P, Ciba Specialty Chemicals Corp.);
5-chloro-2-(2-hydroxy-3,5-di-tert-butylphenyl)-2H-benzotriazole, (TINUVIN® 327, Ciba Specialty Chemicals Corp.);
2-(2-hydroxy-3,5-di-tert-amylphenyl)-2H-benzotriazole, (TINUVIN® 328, Ciba Specialty Chemicals Corp.);
2-(2-hydroxy-3-α-cumyl-5-tert-octylphenyl)-2H-benzotriazole, (TINUVIN® 928, Ciba Specialty Chemicals Corp.);
2,4-di-tert-butylphenyl 3,5-di-tert-butyl4-hydroxybenzoate, (TINUVIN® 120, Ciba Specialty Chemicals Corp.);
2-hydroxy4-n-octyloxybenzophenone, (CHIMASSORB® 81, Ciba Specialty Chemicals Corp.);
2,4-bis(2,4-dimethyphenyl)-6-(2-hydroxy4-octyloxyphenyl)-s-triazine, (CYASORB® 1164, Cytec).

The instant invention also pertains to a flame retardant composition which comprises (a) a polymer substrate, preferably a polyolefin, most preferably polypropylene, and (b) an effective flame retarding amount of a synergistic mixture of (i) a hindered amine of formula A

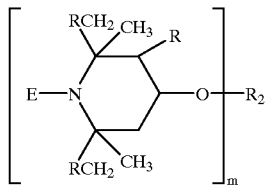 (A)

wherein

E is alkoxy of 1 to 18 carbon atoms, cycloalkoxy of 5 to 12 carbon atoms or aralkoxy of 7 to 15 carbon atoms, or E is —O—T—(OH)$_b$, preferably E is methyoxy, propoxy, cyclohexyloxy or octyloxy, most preferably cyclohexyloxy, T is a straight or branched chain alkylene of 1 to 18 carbon atoms, cycloalkylene of 5 to 18 carbon atoms, cycloalkenylene of 5 to 18 carbon atoms, a straight or branched chain alkylene of 1 to 4 carbon atoms substituted by phenyl or by phenyl substituted by one or two alkyl groups of 1 to 4 carbon atoms;

b is 1, 2 or 3 with the proviso that b cannot exceed the number of carbon atoms in T, and when b is 2 or 3, each hydroxyl group is attached to a different carbon atoms of T;

R is hydrogen or methyl, m is 1 to 4, when m is 1, $R_2$ is hydrogen, $C_1$–$C_{18}$alkyl or said alkyl optionally interrupted by one or more oxygen atoms, $C_2$–$C_{12}$alkenyl, $C_6$–$C_{10}$aryl, $C_7$–$C_{18}$aralkyl, glycidyl, a monovalent acyl radical of an aliphatic, cycloaliphatic or aromatic carboxylic acid, or a carbamic acid, preferably an acyl radical of an aliphatic carboxylic acid having 2–18 C atoms, of a cycloaliphatic carboxylic acid having 5–12 C atoms or of an aromatic carboxylic acid having 7–15 C atoms, or

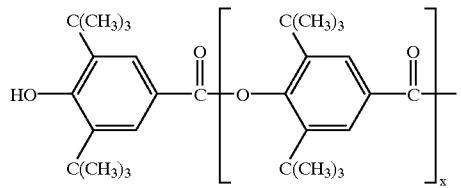

wherein x is 0 or 1,

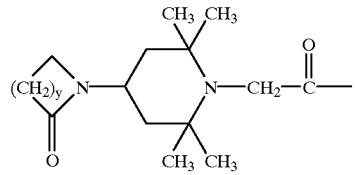

wherein y is 2–4;

when m is 2, $R_2$ is $C_1$–$C_{12}$alkylene, $C_4$–$C_{12}$alkenylene, xylylene, a divalent acyl radical of an aliphatic, cycloaliphatic, araliphatic or aromatic dicarboxylic acid or of a dicarbamic acid, preferably an acyl radical of an aliphatic dicarboxylic acid having 2–18 C atoms, of a cycloaliphatic or aromatic dicarboxylic acid having 8–14 C atoms, or of an aliphatic, cycloaliphatic or aromatic dicarbamic acid having 8–14 C atoms;

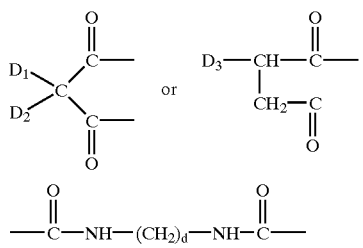

wherein $D_1$ and $D_2$ are independently hydrogen, an alkyl radical containing up to 8 carbon atoms, an aryl or aralkyl radical including 3,5-di-t-butyl-4-hydroxybenzyl radical, $D_3$ is hydrogen, or an alkyl or alkenyl radical containing up to 18 carbon atoms, and d is 0–20;

when m is 3, $R_2$ is a trivalent acyl radical of an aliphatic, unsaturated aliphatic, cycloaliphatic, or aromatic tricarboxylic acid;

when m is 4, $R_2$ is a tetravalent acyl radical of a saturated or unsaturated aliphatic or aromatic tetracarboxylic acid including 1,2,3,4-butanetetracarboxylic acid, 1,2,3,4-but-2-ene-tetracarboxylic, and 1,2,3,5- and 1,2,4,5-pentanetetracarboxylic acid; or wherein the hindered amine compound is a mixture of N,N',N'"-tris{2,4-bis[(1-hydrocarbyloxy-2,2,6,6-tetramethylpiperidin-4-yl)alkylamino]-s-triazin-6-yl}3,3'-ethylenediiminodipropylamine; N,N',N"-tris{2,4-bis[(1-hydrocarbyloxy-2,2,6,6-tetramethylpiperidin-4yl)alkylamino]-s-triazin-6-yl}3,3'-ethylenediiminodipropylamine, and bridged derivatives as described by formulas I, II, IIA and III $R_1NH—CH_2CH_2CH_2NR_2CH_2CH_2NR_3CH_2CH_2CH_2NHR_4$ (I)

$T—E_1—T_1$ (II)

T—E₁ (IIA)

G—E₁—G₁—E₁—G₂ (III)

where in the tetraamine of formula I $R_1$ and $R_2$ are the s-triazine moiety $E_2$; and one of $R_3$ and $R_4$ is the s-triazine moiety $E_2$ with the other of $R_3$ or $R_4$ being hydrogen, $E_2$ is

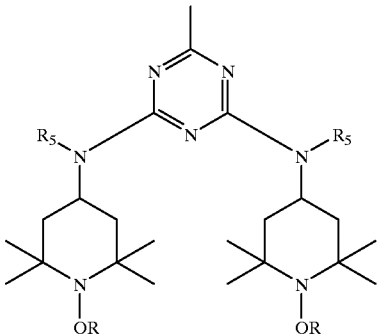

R is methyl, propyl, cyclohexyl or octyl, preferably cyclohexyl, $R_5$ is alkyl of 1 to 12 carbon atoms, preferably n-butyl, where in the compound of formula II or IIA when R is propyl, cyclohexyl or octyl, T and $T_1$ are each a tetraamine substituted by $R_1$–$R_4$ as is defined for formula I, where (1) one of the striazine moieties $E_2$ in each tetraamine is replaced by the group $E_1$ which forms a bridge between two tetraamines T and $T_1$, $E_1$ is

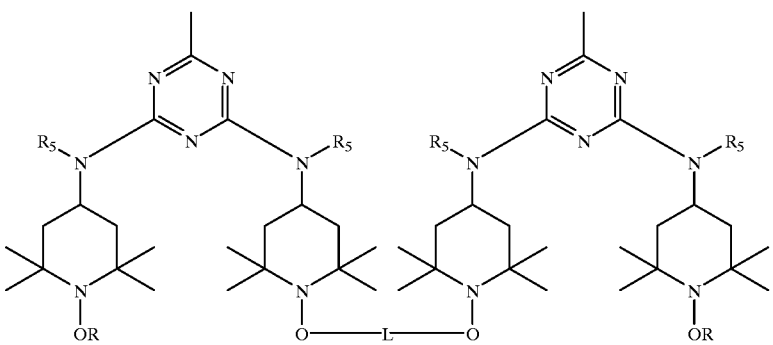

or (2) the group $E_1$ can have both termini in the same tetraamine T as in formula IIA where two of the $E_2$ moieties of the tetraamine are replaced by one $E_1$ group, or (3) all three s-triazine substituents of tetraamine T can be $E_1$ such that one $E_1$ links T and $T_1$ and a second $E_1$ has both termini in tetraamine T, L is propanediyl, cyclohexanediyl or octanediyl;

where in the compound of formula III

G, $G_1$ and $G_2$ are each tetraamines substituted by $R_1$–$R_4$ as defined for formula I, except that G and $G_2$ each have one of the s-triazine moieties $E_2$ replaced by $E_1$, and $G_1$ has two of the triazine moieties $E_2$ replaced by $E_1$, so that there is a bridge between G and $G_1$ and a second bridge between $G_1$ and $G_2$;

which mixture is prepared by reacting two to four equivalents of 2,4-bis[(1-hydrocarbyloxy-2,2,6,6-piperidin-4-yl)butylamino]-6-chloro-s-triazine with one equivalent of N,N'-bis(3-aminopropyl)ethylenediamine;

or the hindered amine is a compound of the formula IIIb

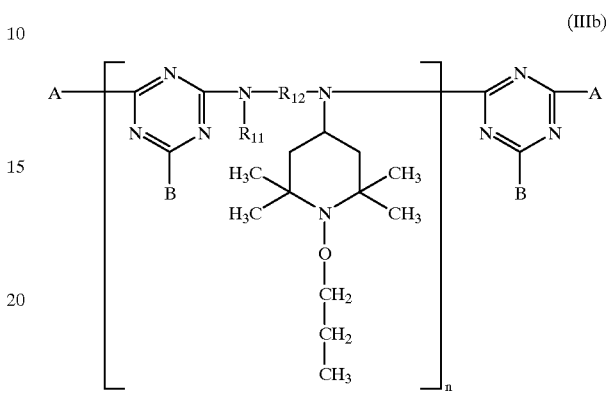

in which the index n ranges from 1 to 15;

$R_{12}$ is $C_2$–$C_{12}$alkylene, $C_4$–$C_{12}$alkenylene, $C_5$–$C_7$cycloalkylene, $C_5$–$C_7$cycloalkylene-di($C_1$–$C_4$alkylene), $C_1$–$C_4$alkylenedi($C_5$–$C_7$cycloalkylene), phenylenedi($C_1$–$C_4$alkylene) or $C_4$–$C_{12}$alkylene interrupted by 1,4-piperazinediyl, —O— or >N—$X_1$ with $X_1$ being $C_1$–$C_{12}$acyl or ($C_1$–$C_{12}$alkoxy)carbonyl or having one of the definitions of $R_{14}$ given below except hydrogen; or $R_{12}$ is a group of the formula (Ib') or (Ic');

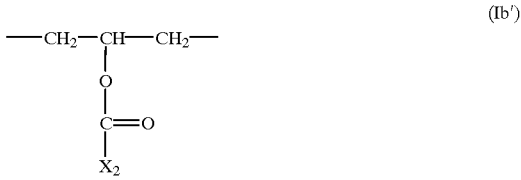

(Ib')

-continued

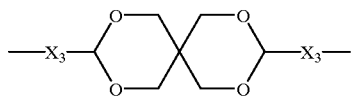
(Ic')

with m being 2 or 3,

X₂ being $C_1$–$C_{18}$alkyl, $C_5$–$C_{12}$cycloalkyl which is unsubstituted or substituted by 1, 2 or 3 $C_1$–$C_4$alkyl; phenyl which is unsubstituted or substituted by 1, 2 or 3 $C_1$–$C_4$alkyl or $C_1$–$C_4$alkoxy; $C_7$–$C_9$phenylalkyl which is unsubstituted or substituted on the phenyl by 1, 2 or 3 $C_1$–$C_4$alkyl; and the radicals X₃ being independently of one another $C_2$–$C_{12}$alkylene;

$R_{13}$, $R_{14}$ and $R_{15}$, which are identical or different, are hydrogen, $C_1$–$C_{18}$alkyl, $C_5$–$C_{12}$cycloalkyl which is unsubstituted or substituted by 1, 2 or 3 $C_1$–$C_4$alkyl; $C_3$–$C_{18}$alkenyl, phenyl which is unsubstituted or substituted by 1, 2 or 3 $C_1$–$C_4$alkyl or $C_1$–$C_4$alkoxy; $C_7$–$C_9$phenylalkyl which is unsubstituted or substituted on the phenyl by 1, 2 or 3 $C_1$–$C_4$alkyl; tetrahydrofurfuryl or $C_2$–$C_4$alkyl which is substituted in the 2, 3 or 4 position by —OH, $C_1$–$C_8$alkoxy, di($C_1$–$C_4$alkyl)amino or a group of the formula (Ie');

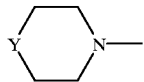
(Ie')

with Y being —O—, —CH₂—, —CH₂CH₂— or >N—CH₃, or —N($R_{14}$)($R_{15}$) is additionally a group of the formula (Ie');

the radicals A are independently of one another —O$R_{13}$, —N($R_{14}$)($R_{15}$) or a group of the formula (IIId);

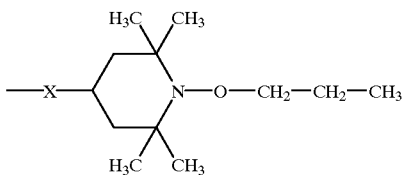
(IIId)

X is —O— or >N—$R_{16}$;
$R_{16}$ is hydrogen, $C_1$–$C_{18}$alkyl, $C_3$–$C_{18}$alkenyl, $C_5$–$C_{12}$cycloalkyl which is unsubstituted or substituted by 1, 2 or 3 $C_1$–$C_4$alkyl; $C_7$–$C_9$phenylalkyl which is unsubstituted or substituted on the phenyl by 1, 2 or 3 $C_1$–$C_4$alkyl; tetrahydrofurfuryl, a group of the formula (IIIf),

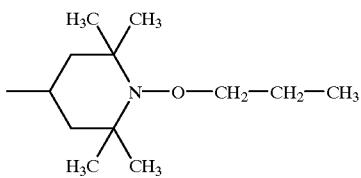
(IIIf)

or $C_2$–$C_4$alkyl which is substituted in the 2, 3 or 4 position by —OH, $C_1$–$C_8$alkoxy, di($C_1$–$C_4$alkyl)amino or a group of the formula (Ie');
$R_{11}$ has one of the definitions given for $R_{16}$; and
the radicals B have independently of one another one of the definitions given for A;
(ii) a brominated and/or a phosphorus containing flame retardant with the proviso that when the polymeric substrate is polypropylene, the flame retardant is not a halogenated hydrocarbyl phosphate or phosphonate.

Preferably the hindered amine compounds are the mixture of compounds of formula I, II, IIA and III where R is cyclohexyl; bis(1-octyloxy-2,2,6,6-tetramethylpiperidin-4yl) sebacate; 1-(2-hydroxy-2-methylpropoxy)4-octadecanoyloxy-2,2,6,6-tetramethylpiperidine, or the compound of formula

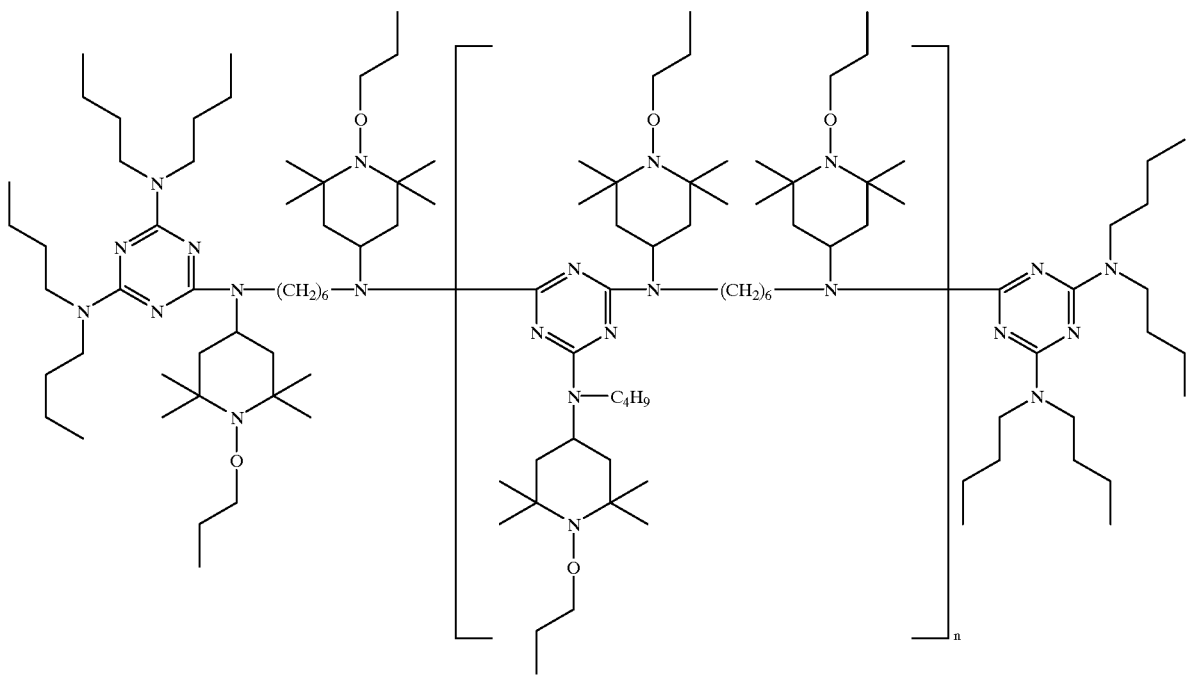

In the structures A to R, if any substituents are $C_1$–$C_{18}$ alkyl, they are for example methyl, ethyl, n-propyl, n-butyl, sec-butyl, tert-butyl, n-hexyl, n-octyl, 2-ethylhexyl, n-nonyl, n-decyl, n-undecyl, n-dodecyl, n-tridecyl, n-tetradecyl, n-hexadecyl or n-octadecyl. Typical cycloalkyl groups include cyclopentyl and cyclohexyl; typical cycloalkenyl groups include cyclohexenyl; while typical aralkyl groups include benzyl, alpha-methyl-benzyl, alpha,alpha-dimethylbenzyl or phenethyl. $C_1$–$C_{12}$ alkyl and cyclohexyl are preferred.

If $R_2$ is a monovalent acyl radical of a carboxylic acid, it is for example an acyl radical of acetic acid, stearic acid, salicyclic acid, benzoic acid or β-(3,5-di-tert-butyl-4-hydroxyphenyl) propionic acid.

If $R_2$ is a divalent acyl radical of a dicarboxylic acid, it is for example an acyl radical of oxalic acid, adipic acid, succinic acid, suberic acid, sebacic acid, phthalic acid dibutylmalonic acid, dibenzylmalonic acid or butyl-(3,5-di-tert-butyl-4-hydropxybenzyl)-malonic acid, or bicycloheptene-dicarboxylic acid, with succinates, sebacates, phthalates and isophthalates being preferred.

If $R_2$ is a divalent acyl radical of a dicarbamic acid, it is for example an acyl radical of hexamethylenedicarbamic acid or of 2,4-toluylenedicarbamic acid.

The instant NOR hindered amine compounds as described above are known in the prior art and are prepared as taught in U.S. Pat. Nos. 5,004,770; 5,096,950; 5,204,473, 5,300, 544 and 5,844,026; and patent application Ser. Nos. 09/253, 161 and 09/257,711.

Preferably, the polymer substrate is selected from the group of resins consisting of the polyolefins, the thermoplastic olefins, styrenic polymers and copolymers, and ABS.

(a) the mixture of compounds of formula I, II, IIA and III where R is cyclohexyl;

(b) 1-cyclohexyloxy-2,2,6,6-tetramethyl-4-octadecylaminopiperidine;

(c) bis(1-octyloxy-2,2,6,6-tetramethylpiperidin-4-yl) sebacate;

(d) 2,4-bis[(1-cyclohexyloxy-2,2,6,6-tetramethylpiperidin-4-yl)butylamino]-6-(2-hydroxyethylamino-s-triazine;

(e) bis(1-cyclohexyloxy-2,2,6,6-tetramethylpiperidin-4-yl) adipate;

(f) the oligomeric compound which is the condensation product of 4,4'-hexamethylene-bis(amino-2,2,6,6-tetramethylpiperidine) and 2,4-dichloro-6-[(1-octyloxy-2,2,6,6-tetramethylpiperidin-4-yl)butylamino]-s-triazine end-capped with 2-chloro-4,6-bis(dibutylamino)-s-triazine;

(g) the oligomeric compound which is the condensation product of 4,4'-hexamethylene-bis(amino-2,2,6,6-tetramethylpiperidine) and 2,4-dichloro-6-[(1-cyclohexyloxy-2,2,6,6-tetra-methylpiperidin-4-yl)butylamino]-s-triazine end-capped with 2-chloro-4,6-bis(dibutylamino)-s-triazine;

(h) 2,4-bis[(1-cyclohexyloxy-2,2,6,6-piperidin-4-yl)butylamino]-6-chloro-s-triazine;

(i) 1-(2-hydroxy-2-methylpropoxy)-4-octadecanoyloxy-2,2,6,6-tetramethylpiperidine; or (j) the compound of formula

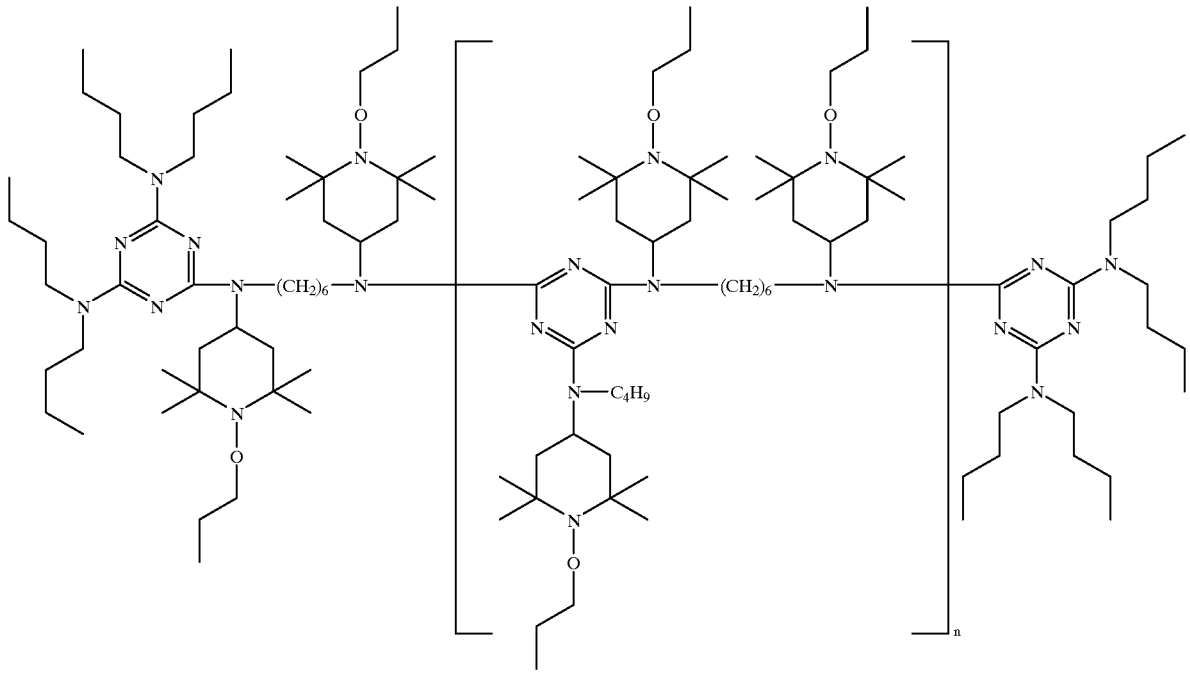

More preferably, the polymer substrate is polypropylene, polyethylene, thermoplastic olefin (TPO), ABS and high impact polystyrene.

Most preferably, polymer substrate is polypropylene, polyethylene or thermoplastic olefin (TPO).

Preferably, the NOR or NOROL hindered amine of component (i) is

Most preferably, the compound of component (i) is (a) the mixture of compounds of formula I, II, IIA and III where R is cyclohexyl;

(c) bis(1-octyloxy-2,2,6,6-tetramethylpiperidin-4-yl) sebacate;

(i) 1-(2-hydroxy-2-methylpropoxy)-4-octadecanoyloxy-2,2,6,6-tetramethylpiperidine; or (j) the compound of formula

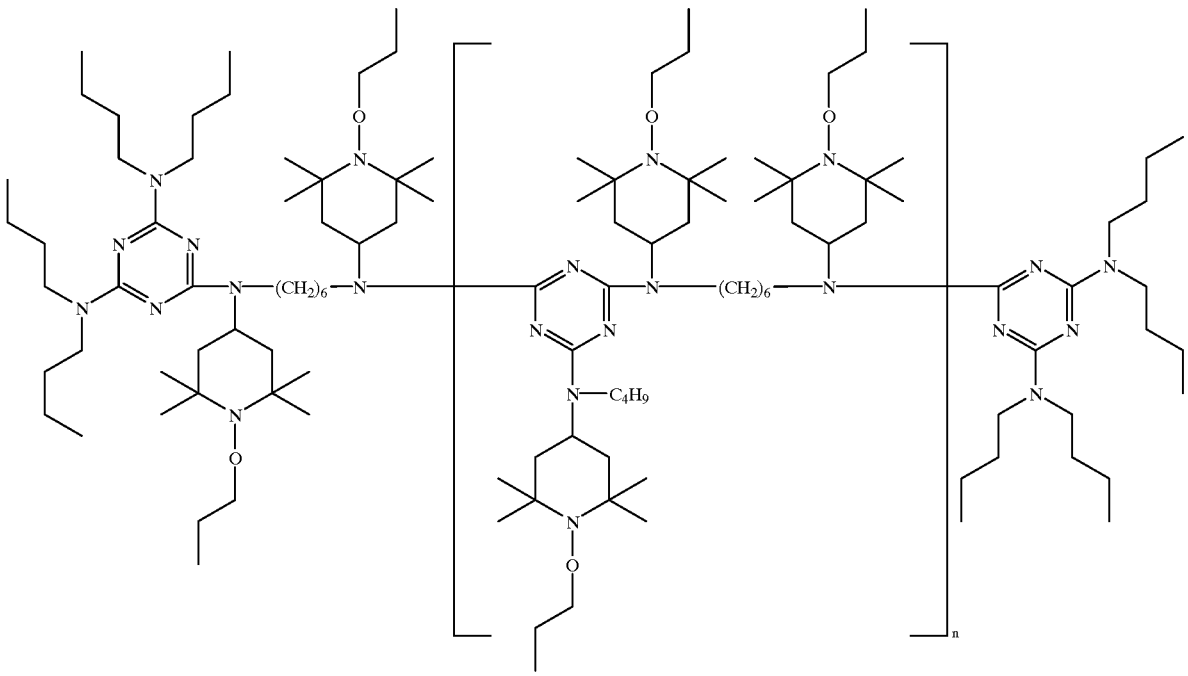

The effective flame retarding amount of the hindered amine is that needed to show flame retarding efficacy as measured by one of the standard methods used to assess flame retardancy. These include the NFPA 701 Standard Methods of Fire Tests for Flame-Resistant Textiles and Films, 1989 and 1996 editions; the UL 94 Test for Flammability of Plastic Materials for Parts in Devices and Appliances, 5th Edition, Oct. 29, 1996; Limiting Oxygen Index (LOI), ASTM D-2863; and Cone Calorimetry, ASTM E-1354.

The effective amount of hindered amine needed to achieve flame retardancy is from 0.05 to 10% by weight based on the polymeric substrate; preferably 0.5 to 8% by weight; and most preferably 0.5 to 2% by weight.

The effective flame retarding amount of the synergistic mixture (b) containing components (i) and (ii) is 0.5 to 30% by weight based on component (a).

In that synergistic mixture (b), the effective flame retarding amount of a hindered amine is 0.5 to 10% by weight based on component (a); and preferably is 0.5 to 8% by weight based on component (a).

More particularly, the flame retardant compounds useful in the instant invention are preferably selected from the group consisting of polybrominated diphenyl oxide (DE-60F, Great Lakes Corp.)
  decabromodiphenyl oxide (DBDPO; SAYTEX® 102E)
  bis(2,3-dibromopropyl ether) of bisphenol A (PE68),
  ammonium polyphosphate (APP) or (HOSTAFLAM® AP750),
  brominated epoxy resin,
  ethylene-bis(tetrabromophthalimide) (BT93),
  1,2-bis(tribromophenoxy)ethane (FF680), and
  tetrabromo-bisphenol A (SAYTEX® RB100).

Coadditives found useful for use with the instant NOR-hindered amine compounds in flame retardant compositions are as follows:

Phosphorus Compounds
  tris(2,4-di-tert-butylphenyl) phosphite, (IRGAFOS® 168, Ciba Specialty Chemicals Corp.);
  bis(2,4-di-tert-butyl-6-methylphenyl) ethyl phosphite, (IRGAFOS® 38, Ciba Specialty Chemicals Corp.);
  2,2',2''-nitrilo[triethyl-tris-(3,3',5,5'-tetra-tert-butyl-1,1'-biphenyl-2,2'-diyl)phosphite], (IRGAFOS® 12, Ciba Specialty Chemicals Corp.);
  tetrakis(2,4-di-butylphenyl) 4,4'-biphenylenediphosphonite, (IRGAFOS® P-EPQ, Ciba Specialty Chemicals Corp.);
  tris(nonylphenyl) phosphite, (TNPP®, General Electric);
  bis(2,4-di-tert-butylphenyl) pentaerythrityl diphosphite, (ULTRANOX® 626, General Electric);
  2,2'-ethylidenebis(2,4-di-tert-butylphenyl) fluorophosphite, (ETHANOX® 398, Ethyl Corp.)
  2-butyl-2-ethylpropan-1,3-diyl 2,4,6-tri-tert-butylphenyl phosphite, (ULTRANOX® 641, General Electric).

Flame Retardants
  tris[3-bromo-2,2-bis(bromomethyl)propyl]phosphate, (PB 370®, FMC Corp.)
  decabromodiphenyl oxide, (DBDPO);
  ethylene bis-(tetrabromophthalimide), (SAYTEX® BT-93);
  ethylene bis-(dibromo-norbornanedicarboximide), (SAYTEX® BN-451)

UV Absorbers
  2-(2-hydroxy-3,5-di-α-cumylphenyl)-2H-benzotriazole, (TINUVIN® 234, Ciba Specialty Chemicals Corp.);
  2-(2-hydroxy-5-methylphenyl)-2H-benzotriazole, (TINUVIN® P, Ciba Specialty Chemicals Corp.);
  5-chloro-2-(2-hydroxy-3,5-di-tert-butylphenyl)-2H-benzotriazole, (TINUVIN® 327, Ciba Specialty Chemicals Corp.);
  2-(2-hydroxy-3,5-di-tert-amylphenyl)-2H-benzotriazole, (TINUVIN® 328, Ciba Specialty Chemicals Corp.);
  2-(2-hydroxy-3-α-cumyl-5-tert-octylphenyl)-2H-benzotriazole, (TINUVIN® 928, Ciba Specialty Chemicals Corp.);

2,4-di-tert-butylphenyl 3,5-di-tert-butyl-4-hydroxybenzoate, (TINUVIN® 120, Ciba Specialty Chemicals Corp.);

2-hydroxy-4-n-octyloxybenzophenone, (CHIMASSORB® 81, Ciba Specialty Chemicals Corp.);

2,4-bis(2,4-dimethyphenyl)-6-(2-hydroxy-4-octyloxyphenyl)-s-triazine, (CYASORB® 1164, Cytec).

The following examples are meant for illustrative purposes only and are not to be construed to limit the scope of this invention in any manner whatsoever.

Test Methods

NFPA 701 Standard Methods of Fire Tests for Flame-Resistant Textiles and Films, 1989 and 1996 editions;

UL 94 Test for Flammability of Plastic Materials for Parts in Devices and Appliances, 5th Edition, Oct. 29, 1996;

Limiting Oxygen Index (LOI), ASTM D-2863;

Cone Calorimetry, ASTM E-1 or ASTM E 1354;

ASTM D 2633–82, burn test.

NOR-6 is the oligomeric compound which is the condensation product of 4,4'-hexamethylene-bis(amino-2,2,6,6-tetramethylpiperidine) and 2,4-dichloro-6-[(1-octyloxy-2,2,6,6-tetramethylpiperidin-4-yl)butylamino]-s-triazine end-capped with 2-chloro-4,6-bis(dibutylamino)-s-triazine.

NOR-7 is the oligomeric compound which is the condensation product of 4,4'-hexamethylene-bis(amino-2,2,6,6-tetramethylpiperidine) and 2,4-dichloro-6-[(1-cyclohexyloxy-2,2,6,6-tetra-methylpiperidin-4-yl)butylamino]-s-triazine end-capped with 2-chloro-4,6-bis(dibutylamino)-s-triazine.

NOR-8 is 2,4-bis[(1-cyclohexyloxy-2,2,6,6-piperidin-4-yl)butylamino]-6-chloro-s-triazine.

NOR-9 is 1-(2-hydroxy-2-methylpropoxy)4-octadecanoyloxy-2,2,6,6-tetramethylpiperidine.

NOR-10 is the compound of formula

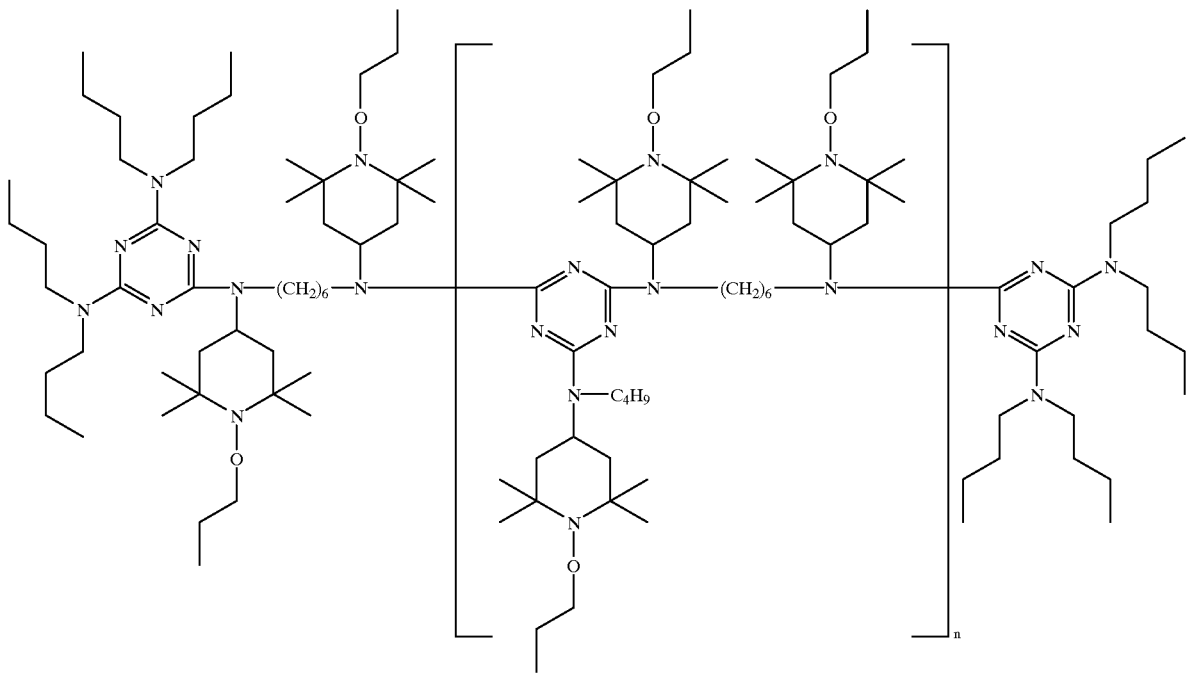

Test Compounds

NOR-1 is the mixture of compounds of formula I, II, IIA and III where R is cyclohexyl.

NOR-2 is 1-cyclohexyloxy-2,2,6,6-tetramethyl-4-octadecylaminopiperidine.

NOR-3 is bis(1-octyloxy-2,2,6,6-tetramethylpiperidin-4-yl) sebacate, (TINUVIN® 123, Ciba Specialty Chemicals Corp.).

NOR-4 is 2,4-bis[(1-cyclohexyloxy-2,2,6,6-tetramethylpiperidin-4-yl)butylamino]-6-(2-hydroxyethylamino-s-triazine.

NOR-5 is bis(1-cyclohexyloxy-2,2,6,6-tetramethylpiperidin-4-yl) adipate.

FR-1 is tris[3-bromo-2,2-bis(bromomethyl)propyl] phosphate, (PB 370®, FMC Corp.).

FR-2 is ammonium polyphosphate (APP).

FR-3 is bis(2,3-dibromopropyl) ether of tetrabromobisphenol A (PE68).

FR-4 is ammonium polyphosphate/synergist blend, HOSTAFLAM® AP750.

FR-5 is decabromodiphenyl oxide, SAYTEX® 102E.

FR-6 is ethylene bis-(tetrabromophthalimide), (SAYTEX® BT-93).

FR-7 is melamine phosphate, MELAPUR® P 46.

FR-8 is ammonium polyphosphate, EXOLIT® AP752.

HA-1 is N,N',N'',N'''-tetrakis[4,6-bis(butyl-1,2,2,6,6-pentamethylpiperidin-4-yl)amino-s-triazin-2-yl]-1,10-diamino-4,7-diazadecane, (CHIMASSORB® 119, Ciba Specialty Chemicals Corp.).

HA-2 is bis(2,2,6,6-tetramethylpiperidin-4-yl) sebacate, (TINUVIN® 770, Ciba Specialty Chemicals Corp.).

EXAMPLE 1

Fiber grade polypropylene, containing 0.05% by weight of calcium stearate and 0.05% of tris(2,4-di-tert-butylphenyl) phosphite and 0.05% of a N,N-dihydroxylamine made by the direct oxidation of N,N-di(hydrogenated tallow)amine is dry blended with the test additives and then melt compounded at 234° C. (450° F.) into pellets. The pelletized fully formulated resin is then spun at 246° C. (475° F.) into fiber using a Hills laboratory model fiber extruder. The spun tow of 41 filaments is stretched at a ratio of 1:3.2 to give a final denier of 615/41.

Socks are knitted from the stabilized polypropylene fiber on a Lawson-Hemphill Analysis Knitter and tested under NFPA 701 vertical burn procedure.

| (weight %) Formulation | Weight Loss % | Drip Burn Time sec | Pass/Fail |
| --- | --- | --- | --- |
| Control | 36 | >50 | Fail |
| FR-5 (4%) | 7 | 0.8 | Pass |
| FR-5 (2%) | 10 | 5 | Fail |
| FR-5 (1%) + NOR-1 (0.5%) | 4 | 0 | Pass |
| FR-5 (1%) + NOR-3 (0.5%) | 9 | 0.5 | Pass |
| FR-5 (1%) + NOR-9 (0.5%) | 5 | 0 | Pass |
| FR-5 (1%) + NOR-10 (0.5%) | 0.1 | 8 | Pass |

In the NFPA 701 test, a vertical piece of fabric is ignited with a Meeker burner. The flame is held on the fabric for 45 seconds. The drip burn time and the fabric weight loss are measured after the burning. To pass the NFPA 701 test, a material should loose less than 40% of weight and have a drip bum time of less than 2 seconds.

FR-5 at the 2% level fails the NFPA 701 test, but even at half that concentration in the presence of the instant hindered amines the flame retardancy performance is vastly improved.

It is clear that when some of the decabromodiphenyl oxide is replaced with a selected hindered amine that flame retardancy is actually enhanced even at a lower total concentration (2% versus 1.5%) enough to pass the NFPA 701 test.

The combination of decabromodiphenyl oxide and the selected hindered amine is synergistic. This result is both surprising and unexpected as well as allowing a lesser amount of a brominated compound to be used and still obtain adequate flame retardancy.

EXAMPLE 2

Polypropylene, the base resin containing 0.05% by weight of calcium stearate, 0.1% by weight of tris(2,4-di-tert-butylphenyl) phosphite and 0.05% by weight of neopentanetetrayl tetrakis(3,5-di-tert-butyl-4-hydroxyhydrocinnamate), is melt compounded on a single-screw extruder at 425° F. (218° C.) with the respective additives to form the formulations given in the table below. 125 mil plaques are compression molded at 400° F.(204° C.).

The plaques are tested for flame retardancy by the UL 94V thick section test.

| Formulation | 1st Flame Time (average seconds) | 2nd Flame Time (average seconds) |
| --- | --- | --- |
| FR-4 (5%) | 252 | ** |
| FR-4 (10%) | 103 | ** |
| FR-4 (5%) + NOR-1 (5%) | 3 | 83 |
| FR-4 (10%) + NOR-1 (5%) | 5 | 4 |
| FR-4 (25%) | 7 | 11 |

**no time is shown for the 2nd flame since the sample is completely consumed after application of the first flame.

It is clear that the combination of the hindered amine NOR-1 with inorganic flame retardant at the same total concentration potentiates the effectiveness of the inorganic flame retardant allowing for a lower concentration of said inorganic flame retardant to be used when combined with the hindered amine component. This is a synergistic effect.

Even when the inorganic flame retardant is used at very high levels alone, it cannot provide as much flame retardancy as the combination of said flame retardant with the hindered amine at a much lower total concentration.

EXAMPLE 3

Following the procedure of Example 2, molding grade polypropylene is dry blended with the test additives and then melt compounded at 425° F. (218° C.). Plaques (125 mil) are prepared by injection molding from the formulations using a Boy Injection Molder at 475° F. (246° C.). The specimens are tested for flame retardancy according to the UL-94 vertical burn test specifications. The results are shown below.

| (weight %) Formulation | First Flame Time (av seconds) | Second Flame Time (av seconds) |
| --- | --- | --- |
| control | 194 | ** |
| FR-5 (10.5%) | 97 | 55 |
| FR-5 (10.5%) + Sb$_2$O$_3$ (3.5%) | 27 | 3 |
| FR-5 (5%) + NOR-1 (0.25%) | 22 | 11 |
| FR-5 (5%) + NOR-9 (0.25%) | 12 | 8 |
| FR-5 (5%) + NOR-10 (0.25%) | 8 | 18 |

**no time is shown for the 2nd flame since the sample is completely consumed after application of the first flame.

FR-5 at the 10.5% level does not provide adequate flame retardancy. However, when only half as much FR4 (5% level) is combined with a very small amount of an instant hindered amines (0.25%), the flame retardancy is greatly improved.

These data show that antimony oxide can be replaced with a small amount of an instant hindered amine in order to achieve good flame retardancy. This is important since the replacement of heavy metals is of prime concern for safety and environmental reasons.

EXAMPLE 4

Polyethylene fibers are prepared from fiber grade polyethylene by dry blending with test additives and melt compounding at 400° F. Fibers are extruded from this formulation using a Hills laboratory scale fiber extruder. Socks are knitted from the fibers and are tested for flame retardancy according to NFPA 701 vertical burn method. Polyethylene fibers contain an instant hindered amine compound in combination with a classic brominated flame retardant decabromodiphenyl oxide (DBDPO); bis(2,3-dibromopropyl) ether of tetrabromobis phenol A (PE68); or ethylene bis-tetrabromophthalimide (SAYTEX® BT-93). These formulated fibers are tested for flame retardancy according to NFPA 701.

The fibers containing both an instant hindered amine compound and a classic brominated flame retardant exhibit enhanced flame retardancy compared to the classic flame retardant alone.

EXAMPLE 5

Polyethylene (LDPE) is melt compounded on a twin screw extruder at 450° F. (232° C.) with the respective additives to form the formulations given in the table below. 125 mil plaques are compression molded at 400° F. (204° C.).

The plaques are tested for flame retardancy by the UL 94V thick section test.

| Formulation | 1st Flame Time (average seconds) | 2nd Flame Time (average seconds) |
|---|---|---|
| Blank | 163 | |
| FR-4 (10%) | 198 | ** |
| FR-4 (5%) + NOR-1 (5%) | 118 | — |
| FR-4 (10%) + NOR-1 (5%) | 1 | 64 |

**no time is shown for the 2nd flame since the sample is completely consumed after the application of the first flame.

It is clear that the combination of the hindered amine NOR-1 with inorganic flame retardant at the same total concentration potentiates the effectiveness of the inorganic flame retardant allowing for a lower concentration of said inorganic flame retardant to be used when combined with the hindered amine component. This is a synergistic effect.

EXAMPLE 6

Foam grade polyethylene is dry blended with test additives and then melt compounded into pellets. The pelletized fully formulated resin is then blown into foam.

The polyethylene foam prepared contains an instant NOR or NOROL compound in combination with a classic brominated flame retardant. The formulated foam is tested for flame retardancy according to the UL-94 burn test method.

The foam containing both an NOR or NOROL compound and a classic brominated flame retardant exhibits enhanced flame retardancy compared to foam containing the classic halogenated flame retardant alone.

EXAMPLE 7

Wire & cable grade polyethylene is dry blended with test additives and then melt compounded into pellets. The pelletized fully formulated resin is then extruded onto wire.

Test specimens are tested for flame retardancy using the ASTM D 2633-82 burn test conditions. The formulations containing both an NOR or NOROL compound and a classic brominated flame retardant exhibits enhanced flame retardancy compared to the classic halogenated flame retardant alone.

EXAMPLE 8

Fiber grade polyethylene is dry-blended with test additives. In addition to a hindered amine, selected flame retardants are also included in the various formulations. Non-woven fabrics are produced from the polymer blend formulations by a spun-bonded or melt-blown process.

The non-woven fabrics made thereby are tested for flame retardancy according to the NFPA 701 vertical burn test specifications. The fabrics containing the hindered amine compounds and selected flame retardants exhibit flame retardancy.

EXAMPLE 9

Fiber grade polypropylene is dry-blended with test additives. In addition to a hindered amine, selected brominated flame retardants are also included in the various formulations. Non-woven fabrics are produced from the polymer blend formulations by a spun-bonded or melt-blown process.

The non-woven fabrics made thereby are tested for flame retardancy according to the NFPA 701 vertical burn test specifications. The fabrics containing the hindered amine compounds and selected brominated flame retardants exhibit flame retardancy.

EXAMPLE 10

Molding grade polystyrene is dry-blended with test additives and then melt compounded. In addition to the hindered amines, selected brominated flame retardants are also included in the test formulations. Specimens are injection molded from these test formulations.

The specimens are tested for flame retardancy according to the UL-94 burn test specifications. The molded specimens containing the hindered amine compounds and selected brominated flame retardants exhibit flame retardancy.

EXAMPLE 11

Foam grade polystyrene is dry-blended with test additives and then melt compounded. In addition to the hindered amines, selected brominated flame retardants are also included in these test formulations. Foam polystyrene specimens are prepared from these test formulations.

The specimens are tested for flame retardancy according to the UL-94 burn test specifications. The foam specimens containing the hindered amine compounds and brominated flame retardants exhibit flame retardancy.

EXAMPLE 12

Molding grade ABS is dry blended with the test additives and then melt compounded at 425° F. (218° C.). Specimens 125 mil (⅛") thick are then injection molded from this formulation using a Boy Injection Molder at 450° F. (232° C.). The specimens are tested for flame retardancy according to the UL-94 vertical burn test specifications. The results are tabulated below.

| (weight %) Formulation | 1st Flame Time (average seconds) | 2nd Flame Time (average seconds) |
|---|---|---|
| control | 141 | ** |
| FR-5 (5%) | 68 | 18 |
| FR-5 (10%) | 42 | 28 |

-continued

| (weight %) Formulation | 1st Flame Time (average seconds) | 2nd Flame Time (average seconds) |
|---|---|---|
| FR-5 (7.5%) + NOR-1 (0.25%) | 30 | 13 |
| FR-5 (5%) + NOR-1 (0.25%) | 39 | 20 |

**no time is shown for the 2nd flame since the sample is completely consumed after application of the first flame.

It is clear that the combination of the hindered amine NOR-1 with an organic flame retardant at essentially the same total concentration potentiates the effectiveness of the organic flame retardant allowing for a lower concentration of said organic flame retardant to be used when combined with the hindered amine component. This is a synergistic effect.

Even when the organic flame retardant is used at very high levels alone, it cannot provide as much flame retardancy as the combination of said flame retardant with the hindered amine at a much lower total concentration.

EXAMPLE 13

Following the general procedure of Example 2, molding grade polypropylene is dry blended with the test additives and then melt compounded at 425° F. (218° C.). Specimens 125 mil (1/8") thick are then injection molded from this formulation at 450° F. (232° C.). The specimens are tested for flame retardancy according to the UL-94 horizontal burn test specifications. The results are tabulated below.

| (weight %) Formulation | Burn Time (seconds) | | | |
|---|---|---|---|---|
| | Specimen 1 | Specimen 2 | Specimen 3 | Total |
| FR-7 (5%) | 186 | 182 | 180 | 548 |
| FR-7 (5%) + NOR-1 (0.5%) | 3 | 35 | 25 | 63 |
| FR-7 (2.5%) + NOR-1 (1%) | 132 | 13 | 24 | 169 |
| FR-7 (2.5%) + NOR-10 (1%) | 2 | 1 | 1 | 4 |
| FR-8 (10%) | 282 | 271 | 172 | 725 |
| FR-8 (5%) + NOR-1 (1%) | 3 | 8 | 5 | 16 |
| FR-8 (5%) + NOR-10 (1%) | 2 | 1 | 2 | 5 |

It is clear that the combination of the hindered amine NOR-1 or NOR-10 with an inorganic or organic flame retardant at essentially the same and even at a lesser total concentration potentiates the effectiveness of the inorganic or organic flame retardant allowing for a lower concentration of said inorganic or organic flame retardant to be used when combined with the hindered amine component. This is a synergistic effect.

Even when the inorganic or organic flame retardant is used at very high levels alone, it cannot provide as much flame retardancy as the combination of said flame retardant with the hindered amine at a much lower total concentration.

EXAMPLE 14

Fiber grade polypropylene, containing 0.05% by weight of calcium stearate and 0.05% of tris(2,4-di-tert-butylphenyl) phosphite and 0.05% of a N,N-dihydroxylamine made by the direct oxidation of N,N-di(hydrogenated tallow)amine is dry blended with the test additives and then melt compounded at 234° C. (450° F.) into pellets. The pelletized fully formulated resin is then spun at 246° C. (475° F.) into fiber using a Hills laboratory model fiber extruder. The spun tow of 41 filaments is stretched at a ratio of 1:3.2 to give a final denier of 615/41.

Socks are knitted from the stabilized polypropylene fiber on a Lawson-Hemphill Analysis Knitter and tested under NFPA 701 vertical burn procedure. The time in seconds for the knitted sock to extinguish after the insult flame is removed is reported as "After Flame". Both the maximum time for any one replicate and the total time for all ten replicates are shown in the table below. Efficacy as a flame retardant is demonstrated when low After Flame times are observed relative to a blank sample containing no flame retardant.

| | After Flame (time sec) | |
|---|---|---|
| Formulation | max | total |
| blank | 55 | 177 |
| HA-1 (1%) | 131 | 231 |
| brominated flame retardants | | |
| FR-1 (3%) | 0 | 0 |
| FR-1 (1%) | 10 | 27 |
| NOR-hindered amines | | |
| NOR-1 (1%) | 0 | 0 |
| NOR-2 (1%) | 0 | 0 |
| NOR-3 (1%) | 15 | 43 |

Surprisingly, while conventional hindered amines have at best essentially a neutral effect on flame retardancy, the instant 1-hydrocarbyoxy (NOR) hindered amines are as effective as brominated flame retardants at one third the concentration level. These NOR-hindered amines do not have the detrimental effects associated with inorganic flame retardants.

EXAMPLE 15

Following the procedure set forth in Example 14, stabilized polypropylene fibers are prepared.

Socks are knitted from the stabilized polypropylene fiber on a Lawson-Hemphill Analysis Knitter and tested under NFPA 701 vertical burn procedure. Several other types of hindered amines are compared to the NOR-hindered amines as potential flame retardants using the NFPA 701 test procedure. The results are given in the table below.

| | After Flame (time sec) | |
|---|---|---|
| Formulation | max | total |
| blank | 26 | 69 |
| FR-1 (3%) | 0 | 0 |
| FR-2 (0.5%) | 32 | 70 |
| non NOR-hindered amines | | |
| HA-1 (1%) | 39 | 175 |
| HA-2 (1%) | 52 | 144 |

-continued

| Formulation | After Flame (time sec) | |
|---|---|---|
| | max | total |
| NOR-hindered amines | | |
| NOR-4 (1%) | 0 | 0 |
| NOR-5 (1%) | 0 | 0 |
| NOR-6 (1%) | 6 | 10 |
| NOR-1 (1%) | 0 | 0 |
| NOR-7 (1%) | 0 | 0 |
| NOR-8 (1%) | 0 | 0 |
| NOR-1 (1%) | 0 | 0 |
| NOR-1 (0.5%) | 0 | 0 |
| NOR-1 (0.25%) | 18 | 33 |

It is clear that the NOR-hindered amines are as a group effective as some phosphorus flame retardants in providing flame retardancy to polypropylene fibers, and that they are effective in reducing After Flame at levels as low as 0.25% by weight.

EXAMPLE 16

Molding grade polypropylene is dry blended with test additives and then melt compounded into pellets. The pelletized fully formulated resin is then compression molded into test specimens using a Wabash Compression Molder.

Test plaques are tested under UL-94 Vertical Burn test conditions. The average time in seconds for the test sample to extinguish after the insult flame is removed is reported. Efficacy as a flame retardant is demonstrated when low Flame times are observed relative to the blank sample containing no flame retardant.

All samples containing the instant NOR-hindered amines self-extinguished after application of the first flame. This shows that the instant NOR compounds exhibit discernible efficacy as flame retardants essentially equal to that bestowed by a halogenated or phosphate flame retardant. The blank burned completely after application of the first flame.

| Formulation | 1st Flame (average seconds) |
|---|---|
| blank | 172 |
| FR-3 (1.75%) + Sb$_2$O$_3$ (1%) | 5 |
| FR-4 (25%) | 4 |
| NOR-1 (1%) | 4 |
| NOR-1 (5%) | 4 |
| NOR-1 (10%) | 3 |

EXAMPLE 17

Film grade polyethylene is dry blended with the test additives and then melt compounded into pellets. The pelletized fully formulated resin is then blown at 205° C. using a MPM Superior Blown film extruder.

The films are tested for flame retardancy under NFPA 701 test conditions. The films containing the instant NOR compounds show flame retardancy.

Film grade polypropylene is handled in a similar fashion and polypropylene films containing the instant NOR compounds also show flame retardancy.

EXAMPLE 18

Molded test specimens are prepared by injection molding thermoplastic olefin (TPO) pellets containing a NOR-hindered amine compound. The TPO formulations may also contain a pigment, a phosphite, a phenolic antioxidant or hydroxylamine, a metal stearate, a UV absorber or a hindered amine stabilizer or a mixture of hindered amine and UV absorber.

Pigmented TPO formulation composed of polypropylene blended with a rubber modifier where the rubber modifier is an in-situ reacted copolymer or blended product containing copolymers of propylene and ethylene with or without a ternary component such as ethylidene norbornene are stabilized with a base stabilization system consisting of an N,N-dialkylhydroxylamine or a mixture of hindered phenolic antioxidant and an organophosphorus compound.

The TPO plaques are tested for flame retardancy using the UL-94 Vertical Burn conditions. A minimum of three replicates are tested. Efficacy as a flame retardant is measured relative to a blank sample containing no flame retardant.

The TPO formulations containing an instant NOR-hindered amine show flame retardancy efficacy.

EXAMPLE 19

Film grade ethylene/vinyl acetate (EVA) copolymers containing 20 weight percent or less of vinyl acetate are dry blended with test additives amd then melt compounded into pellets. The pelletized fully formulated resin is then blown into a film at 205° C. using a MPM Superior Blown-film extruder.

The films are tested for flame retardancy under NFPA 701 test conditions. The films containing the instant NOR-hindered amine compounds show flame retardancy.

Film grade low density polyethylene (LDPE) which contains some linear low density polyethylene (LLDPE) and/or ethylene/vinyl acetate (EVA) are dry blended with test additives and blown into film as described above for EVA copolymer resin. The films are tested for flame retardancy under NFPA 701 test conditions and those containing the instant NOR-hindered amines show flame retardancy.

EXAMPLE 20

Fiber grade polypropylene is dry blended with test additives and then melt compounded at 400° F. In addition to the instant NOR-hindered amine compounds, halogenated flame retardants are included in the formulations. Typical formulations contain the instant NOR compounds and a flame retardant such as bis(2,3-dibromopropyl) ether of bisphenol A (PE68), decabromodiphenyloxide (DBDPO), ethylene bis-tetrabromophthalimide (SAYTEX BT-93) or ethylene bis-dibromonorbornanedicarboximide (SAYTEX BN451). Other formulations may contain antimony trioxide in addition to brominated flame retardants. Other formulations may contain phosphorus based flame retardants such as ethylenediamine diphosphate (EDAP) or ammonium polyphosphate (APP).

Fibers are extruded from these formulations using a Hills laboratory scale fiber extruder at 475° F. Socks are knitted from these fibers and tested for flame retardancy according to the NFPA 701 vertical burn test conditions. The fibers containing the NOR-hindered amine compounds show flame retardancy.

EXAMPLE 21

Molding grade polypropylene is dry blended with test additives and then melt compounded into pellets. In addition to the instant NOR-hindered amine compounds selected flame retardants are also included. The pelletized fully formulated resin is then compression molded into test specimens using a Wabash Compression Molder.

Test plaques are tested under UL-94 Vertical Burn conditions. A minimum of three replicates are tested. The average time in seconds for the test sample to extinguish after a first and second insult flame is removed is reported. Efficacy as a flame retardant is demonstrated when low Flame times are observed.

| Formulation | 1st Flame Time (average seconds) | 2nd Flame Time (average seconds) |
|---|---|---|
| blank | 172 | ** |
| FR-3 (1.75%) + Sb$_2$O$_3$ (1%) | 5 | 22 |
| FR-3 (1.75%) + Sb$_2$O$_3$ (1%) + NOR-1 (5%) | 2 | 1 |
| FR-4 (10%) | 103 | ** |
| FR-4 (10%) + NOR-1 (5%) | 5 | 4 |

**no time is shown for the 2nd flame since the sample is completely consumed after application of the first flame.

All samples containing the instant NOR compound along with a flame retardant self-extinguish after application of the first and second flames. Additionally, the time of burning decreases significantly in comparison to the formulation containing flame retardant alone. This shows that the instant NOR compounds enhance the flame retardancy of a halogenated or phosphate flame retardant.

EXAMPLE 22

Molded test specimens are prepared by injection molding thermoplastic olefin (TPO) pellets as described in Example 18. Typical formulations contain the instant NOR compounds and a flame retardant such as tris[3-bromo-2,2,-bis(bromomethyl)propyl]phosphate (PB370), bis(2,3-dibromopropyl) ether of tetrabromobisphenol A (PE68), decabromodiphenyloxide (DBDPO), ethylene bis-tetrabromophthalimide (SAYTEX BT-93) or ethylene bis-dibromonorbornanedicarboximide (SAYTEX BN451). Other formulations may contain antimony trioxide in addition to brominated flame retardants. Other formulations may contain phosphorus based flame retardants such as ethylenediamine diphosphate (EDAP).

Plaques are tested under the UL-94 test method. A minimum of three replicates are tested. The average time in seconds for the test sample to extinguish after a first and second insult flame is removed is reported. The instant NOR-hindered amine compounds enhance the flame retardancy of a halogenated or phosphate flame retardant compared to when the flame retardant is used alone.

EXAMPLE 23

Film grade polyethylene is dry blended with test additives and then melt compounded and into pellets. In addition to the instant NOR-hindered amine compounds, flame retardants are also included in the formulation. Typical formulations contain the NOR compounds and a flame retardant such as bis(2,3-dibromopropyl) ether of tetrabromobisphenol A (PE68), decabromodiphenyloxide (DBDPO) or ethylene bis-tetrabromophthalimide (SAYTEX BT-93). Other formulations may contain antimony trioxide in addition to brominated flame retardants. Other formulations may contain phosphorus based flame retardants such as ethylenediamine diphosphate (EDAP) or ammonium polyphosphate (APP). The pelletized fully formulated resin is then blown into film at 205° C. using a Superior Blown-film extruder.

The test specimens are tested under NFPA 701 test conditions. The instant NOR-hindered amines enhance the flame retardancy of a halogenated or phosphate flame retardant.

EXAMPLE 24

Thermoplastic resins including polypropylene, polyethylene homopolymer, polyolefin copolymer or thermoplastic olefins (TPO), high impact polystyrene (HIPS) and ABS are dry blended with the instant NOR compounds and then melt compounded into pellets. The pelletized fully formulated resin is then processed into a useful article such as extrusion into fiber; blown or cast extrusion into film; blow molded into bottles; injection molded into molded articles, thermoformed into molded articles, extruded into wire and cable housing or rotation molded into hollow articles.

The articles containing the instant NOR compounds exhibit flame retardancy when tested by a known standard test method for assessing flame retardancy.

Polyethylene wire and cable applications are tested for flame retardancy according to ASTM D-2633-82 burn test method. The materials containing the instant NOR compounds show flame retardancy.

EXAMPLE 25

Articles prepared according to Example 24 which additionally contain an organophosphorus stabilizer selected from the group consisting of tris(2,4-di-tert-butylphenyl) phosphite, bis(2,4-di-tert-butyl-6-methylphenyl) ethyl phosphite, 2,2',2"-nitrilo[triethyl-tris-(3,3',5,5'-tetra-tert-butyl-1,1'-biphenyl-2,2'-diyl) phosphite], tetrakis(2,4-di-butylphenyl) 4,4'-biphenylenediphosphonite, tris (nonylphenyl) phosphite, bis(2,4-di-tert-butylphenyl) pentaerythrityl diphosphite, 2,2'-ethylidenebis(2,4-di-tert-butylphenyl) fluorophosphite and 2-butyl-2-ethylpropan-1, 3-diyl 2,4,6-tri-tert-butylphenyl phosphite as well as the instant NOR-hindered amine compounds exhibit good flame retardancy properties.

EXAMPLE 26

Articles prepared according to Example 24 which additionally contain a o-hydroxyphenyl-2H-benzotriazole, a hydroxyphenyl benzophenone or a o-hydroxyphenyl-s-triazine UV absorber selected from the group consisting of 2-(2-hydroxy-3,5-di-α-cumylphenyl)-2H-benzotriazole, 2-(2-hydroxy-5-methylphenyl)-2H-benzotriazole, 5-chloro-2-(2-hydroxy-3,5-di-tert-butylphenyl)-2H-benzotriazole, 2-(2-hydroxy-3,5-di-tert-amylphenyl)-2H-benzotriazole, 2-(2-hydroxy-3-α-cumyl-5-tert-octylphenyl)-2H-benzotriazole, 2,4-di-tert-butylphenyl 3,5-di-tert-butyl-4-hydroxybenzoate, 2-hydroxy4-n-octyloxybenzophenone and 2,4-bis(2,4-dimethyphenyl)-6-(2-hydroxy-4-octyloxyphenyl)-s-triazine as well as the instant NOR-hindered amine compounds exhibit good flame retardancy.

EXAMPLE 27

Articles prepared according to Example 24 which additionally contain a o-hydroxyphenyl-2H-benzotriazole, a hydroxyphenyl benzophenone or a o-hydroxyphenyl-s-triazine UV absorber selected from the group consisting of 2-(2-hydroxy-3,5-di-α-cumylphenyl)-2H-benzotriazole, 2-(2-hydroxy-5-methylphenyl)-2H-benzotriazole, 5-chloro-2-(2-hydroxy-3,5-di-tert-butylphenyl)-2H-benzotriazole, 2-(2-hydroxy-3,5-di-tert-amylphenyl)-2H-benzotriazole, 2-(2-hydroxy-3-α-cumyl-5-tert-octylphenyl)-2H-benzotriazole, 2,4-di-tert-butylphenyl 3,5-di-tert-butyl-4-hydroxybenzoate, 2-hydroxy-4-n-octyloxybenzophenone and 2,4-bis(2,4-dimethyphenyl)-6-(2-hydroxy-4-octyloxyphenyl)-s-triazine as well as the instant NOR-hindered amine compounds and a flame retardant such as tris[3-bromo-2,2,-bis(bromomethyl)propyl]phosphate (PB370), bis(2,3-dibromopropyl) ether of tetrabromo-bisphenol A (PE68), decabromodiphenyloxide (DBDPO), ethylene bis-tetrabromophthalimide (SAYTEX BT-93) or ethylene bis-dibromonorbornanedicarboximide (SAYTEX BN-451) exhibit good flame retardancy properties.

Other formulations may contain antimony trioxide in addition to brominated flame retardants. Other formulations may contain phosphorus based flame retardants such as ethylenediamine diphosphate (EDAP).

EXAMPLE 28

ABS polymer (Dow 342EZ) is blended with the test stabilizers and additives, and compounds on a twin screw extruder at a die temperature of 220° C. and the extrudate is pelletized. The pellets are injection molded on a BOY 50 machine to produce bars of dimensions 5" L×0.5" W×0.125" D. Optionally, the ABS pellets are compression molded at 220° C. to produce test plaques of 4" L×4" W×0.125" D for cone calorimetry testing.

Cone calorimetry testing of the compression molded plaques is carried out according to ASTM E 1354. The results of the tests are shown below.

| Sample*→→ | A | | B | | C | | D | |
|---|---|---|---|---|---|---|---|---|
| | Run 1 | Run 2 | Run 1 | Run 2 | Run 1 | Run 2 | Run 1 | Run 2 |
| PHRR | 1240 | 1273 | 1007 | 1085 | 1209 | 1265 | 1200 | 1265 |
| Ave HRR | 740 | 745 | 393 | 394 | 652 | 653 | 435 | 476 |
| Total HR | 97 | 96 | 44 | 47 | 86 | 85 | 48 | 53 |
| Ave CO y | 0.1 | 0.1 | 0.1 | 0.1 | 0.1 | 0.1 | 0.1 | 0.1 |
| Ave CO$_2$y | 2.4 | 2.4 | 0.8 | 0.9 | 2.3 | 2.3 | 1.4 | 1.5 |

*PHRR - peak heat release rate
Ave HRR - the average heat release rate over the time of the test
Total HR - total heat evolved (area under the calorimetry curve)
Ave CO y - average carbon monoxide yield
Ave CO$_2$y - average carbon dioxide yield Sample A is blank with no flame retardant present.
Sample B contains 15 parts by weight of FR-5 and 4 parts by weight of antimony trioxide.
Sample C contains 4 parts by weight of NOR-1.
Sample D contains 15 parts by weight of FR-5 and 4 parts by weight of NOR-1.

Inspection of the results in the table shows that Sample C containing the NOR-1 gives an unexpected reduction in average heat release rate and reduction in total heat release compared to the unstabilized ABS blank of Sample A.

Nearly equivalent values of average heat release rate and total heat release are observed when comparing a commerical FR system as seen in Sample B with the a combination of FR-5 and NOR-1 as seen in Sample D. In this case the instant NOR-1 compound is used to replace antimony oxide. This is advantageous to remove a heavy metal (antimony) from the system and not to sacrifice the excellent flame retardant performance that can be achieved with the state-of-the-art FR system.

EXAMPLE 29

Following the general procedure of Example 28, high impact polystyrene (HIPS) polymer (STYRON® 484C, Dow Chemical Co.) is compounded with the instant NOR-hindered amine, pelletized and then injection or compression molded into plaques. These plaques are tested for flame retardant efficacy using cone calorimetry, LOI or UL-94 test method.

The plaques containing the NOR compound exhibit flame retardancy. Flame retardant HIPS polymers find application in housings for business machines.

EXAMPLE 30

This Example shows the efficacy of the instant NOR compounds in PVC formulations. Such formulations are useful in flexible or rigid PVC and in wire and cable applications.

Typical formulations are seen below:

| Component | parts | parts | parts | parts |
|---|---|---|---|---|
| PVC resin | 100 | 100 | 100 | 100 |
| tin mercaptide | 1.5 | — | 2.0 | — |
| tin carboxyate | — | 2.5 | — | 2.0 |
| process aid | 1.5 | 1.5 | 2.0 | 2.0 |
| impact mod. | 6.0 | 6.0 | 7.0 | 7.0 |
| paraffin wax | 1.0 | 0.3 | 1.0 | 1.0 |
| polyethyl wax | 0.1 | 0.1 | 0.2 | 0.2 |

-continued

| Component | parts | parts | parts | parts |
|---|---|---|---|---|
| Ca stearate | 1.0 | — | 0.8 | — |
| pigment | 1.0 | 0.9 | 5.0 | 5.0 |

Fully formulated PVC containing the NOR compound is pelletized and then injection molded into test plaques for examination of flame retardancy using the UL-94 or LOI test method.

The PVC plaques containing the instant NOR compound demonstrate flame retardancy.

EXAMPLE 31

Polypropylene, the base resin containing 0.05% by weight of calcium stearate, 0.1% by weight of tris(2,4-di-tert-butylphenyl) phosphite and 0.05% by weight of neopentanetetrayl tetrakis(3,5-di-tert-butyl-4-hydroxyhydrocinnamate), is melt compounded on a single-screw extruder at 425° F. (218° C.) with the respective additives to form the formulations given in the table below. 125 mil plaques are compression molded at 400° F. (204° C.).

The plaques are tested for flame retardancy by the UL 94V thick section test.

| Formulation | 1st Flame Time (average seconds) | 2nd Flame Time (average seconds) |
|---|---|---|
| FR-4 (5%) | 252 | ** |
| FR-4 (10%) | 103 | ** |
| FR-4 (5%) + NOR-1 (5%) | 3 | 83 |
| FR-4 (10%) + NOR-1 (5%) | 5 | 4 |
| FR-4 (25%) | 7 | 11 |

** no time is shown for the 2nd flame since the sample is completely consumed after application of the first flame.

It is clear that the combination of the hindered amine NOR-1 with inorganic flame retardant at the same total concentration potentiates the effectiveness of the inorganic flame retardant allowing for a lower concentration of said inorganic flame retardant to be used when combined with the hindered amine component. This is a synergistic effect.

Even when the inorganic flame retardant is used at very high levels alone, it cannot provide as much flame retardancy as the combination of said flame retardant with the hindered amine at a much lower total concentration.

EXAMPLE 32

Following the procedure of Example 31, polypropylene 10 mil films are compression molded from the flame retardant formulations at 400° F. (204° C.). These films are tested for flame retardancy using the 1989 and 1996 NFPA 701 test.

| 1996 NFPA 701 Test | | | |
|---|---|---|---|
| Formulation | Burn Drips | Weight Loss | Pass/Fail |
| Pass Criteria | <2 sec | <40% | |
| Blank | >2 sec | 39% | Fail |
| NOR-1 (1%) | <2 sec | 7% | Pass |
| NOR-1 (5%) | >2 sec | 31% | Fail |
| NOR-1 (10%) | >2 sec | 57% | Fail |

| 1989 NFPA 701 Test | | | | |
|---|---|---|---|---|
| Formulation | After Flame | Burn Drips | Char Length | Pass/Fail |
| Pass Criteria | <2 sec | 0 sec | <5.5 in. | |
| Blank | 28 sec | >2 sec | 10 in | Fail |
| NOR-1 (1%) | <2 sec | 0 sec | 3.4 in | Pass |
| NOR-1 (5%) | 24 sec | >2 sec | 9.3 in | Fail |
| NOR-1 (10%) | 21 sec | >2 sec | 10 in | Fail |

EXAMPLE 33

Fiber grade polyethylene is dry blended with test additives and melt compounded at 400° F. Fibers are extruded from this formulation using a Hills laboratory scale fiber extruder. Socks are knitted from the fibers and are tested for flame retardancy according to NFPA 701 vertical burn method.

The fibers containing the instant NOR compounds show flame retardancy.

EXAMPLE 34

Polyethylene fibers prepared as seen in Example 33 contain an instant NOR compound in combination with a classic flame retardant such as decabromodiphenyl oxide (DBDPO); bis(2,3-dibromopropyl) ether of tetrabromobisphenol A (PE68); ethylene bis-tetrabromophthalimide (SAYTEX® BT-93) and the like. These formulated fibers are tested for flame retardancy according to NFPA 701.

The fibers containing both an NOR compound and a classic halogenated or phosphorus flame retardant exhibit enhanced flame retardancy compared to the classic flame retardant alone.

EXAMPLE 35

Polyethylene (LDPE) is melt compounded on a twin screw extruder at 450° F. (232° C.) with the respective additives to form the formulations given in the table below. 125 mil plaques are compression molded at 400° F.(204° C.).

The plaques are tested for flame retardancy by the UL 94V thick section test.

| Formulation | 1st Flame Time (average seconds) | 2nd Flame Time (average seconds) |
|---|---|---|
| Blank | 163 | |
| NOR-1 (1%) | 149 | |
| NOR-1 (5%) | 124 | |
| FR-6 (3%) + Sb$_2$O$_3$ (1%) | 1 | 250 |
| FR-6 (3%) + Sb$_2$O$_3$ (1%) + NOR-1 (5%) | 11 | 8 |
| FR-4 (10%) | 198 | ** |
| FR-4 (5%) + NOR-1 (5%) | 118 | — |
| FR-4 (10%) + NOR-1 (5%) | 1 | 64 |

** no time is shown for the 2nd flame since the sample is completely consumed after the application of the first flame.

It is clear that the combination of the hindered amine NOR-1 with inorganic flame retardant at the same total concentration potentiates the effectiveness of the inorganic flame retardant allowing for a lower concentration of said inorganic flame retardant to be used when combined with the hindered amine component. This is a synergistic effect.

EXAMPLE 36

Polyethylene (LDPE) is melt compounded on a twin screw extruder at 450° F. (232° C.) with the respective additives to form the formulations given in the table below. 2 mil thick films are blown on a MPM extruder at 400° F. (204° C.).

The films are tested for flame retardancy by the 1989 NFPA 701 test.

| 1989 NFPA 701 Test | | | | |
|---|---|---|---|---|
| Formulation | After Flame | Burn Drips | Char Length | Pass/Fail |
| Pass Criteria | <2 sec | 0 sec | <5.5 in. | |
| Blank | 0–14 sec | 0–2 sec | 8.5 in | Fail |
| NOR-1 (1%) | 0 sec | 0 sec | 4.8 in | Pass |

-continued

1989 NFPA 701 Test

| Formulation | After Flame | Burn Drips | Char Length | Pass/Fail |
|---|---|---|---|---|
| NOR-1 (5%) | 0 sec | 0 sec | 4.8 in | Pass |
| NOR-1 (10%) | 0 sec | 0 sec | 7.9 in | Fail |

EXAMPLE 37

Fiber grade poly(ethylene terephthalate) (PET) is dry blended with test additives, then melt compounded at 550° F. and then pelletized. The polyester pellets are dried at 175° F. for 24 hours under vacuum. The dried pellets are extruded into fibers using a Hills laboratory scale fiber extruder at 550° F. Socks are knitted from these fibers and tested for flame retardancy according to NFPA 701 test method.

The polyester fibers containing the instant NOR hindered amine compound show flame retardancy.

EXAMPLE 38

Polyester (PET) fibers prepared as seen in Example 37 contain an instant NOR compound in combination with a classic flame retardant. These formulated fibers are tested for flame retardancy according to NFPA 701 vertical burn test method.

The fibers containing both an NOR compound and a classic halogenated or phosphorus flame retardant exhibit enhanced flame retardancy compared to the classic flame retardant alone.

EXAMPLE 39

Foam grade polyethylene is dry blended with test additives and then melt compounded into pellets. The pelletized fully formulated resin is then blown into foam.

Test specimens cut from the foam are tested under the UL-94 burn test specification. The foam containing the instant NOR compound exhibits flame retardancy.

EXAMPLE 40

Polyethylene foam prepared as seen in Example 39 contains an instant NOR compound in combination with a classic flame retardant. The formulated foam is tested for flame retardancy according to the UL-94 burn test method.

The foam containing both an NOR compound and a classic flame retardant exhibits enhanced flame retardancy compared to the classic halogenated or phosphorus flame retardant alone.

EXAMPLE 41

Wire & cable grade polyethylene is dry blended with test additives and then melt compounded into pellets. The pelletized fully formulated resin is then extruded onto wire.

Test specimens are tested for flame retardancy using the ASTM D 2633-82 burn test conditions. The formulations containing the instant NOR compounds show flame retardancy.

EXAMPLE 42

Wire & cable grade polyethylene is dry blended with test additives and then melt compounded into pellets. The pelletized fully formulated resin is then extruded onto wire.

Test specimens are tested for flame retardancy using the ASTM D 2633-82 burn test conditions. The formulations containing both an NOR compound and a classic flame retardant exhibits enhanced flame retardancy compared to the classic halogenated or phosphorus flame retardant alone.

EXAMPLE 43

Fiber grade polyethylene is dry-blended with hindered amine test additives. Non-woven fabrics are produced from the polymer blend formulation by a spun-bonded or melt-blown process.

The non-woven fabrics made thereby are tested for flame retardancy according to the NFPA 701 vertical burn test specifications. The fabrics containing the hindered amine compounds exhibit flame retardancy.

EXAMPLE 44

Fiber grade polyethylene is dry-blended with test additives. In addition to a hindered amine, selected flame retardants are also included in the various formulations. Non-woven fabrics are produced from the polymer blend formulations by a spun-bonded or melt-blown process.

The non-woven fabrics made thereby are tested for flame retardancy according to the NFPA 701 vertical burn test specifications. The fabrics containing the hindered amine compounds and selected flame retardants exhibit flame retardancy.

EXAMPLE 45

Fiber grade polypropylene is dry-blended with hindered amine test additives. Non-woven fabrics are produced from the polymer blend formulation by a spun-bonded or melt-blown process.

The non-woven fabrics made thereby are tested for flame retardancy according to the NFPA 701 vertical burn test specifications. The fabrics containing the hindered amine compounds exhibit flame retardancy.

EXAMPLE 46

Fiber grade polypropylene is dry-blended with test additives. In addition to a hindered amine, selected flame retardants are also included in the various formulations. Non-woven fabrics are produced from the polymer blend formulations by a spun-bonded or melt-blown process.

The non-woven fabrics made thereby are tested for flame retardancy according to the NFPA 701 vertical burn test specifications. The fabrics containing the hindered amine compounds and selected flame retardants exhibit flame retardancy.

EXAMPLE 47

Molding grade polystyrene is dry-blended with hindered amine test additives and then melt compounded. Specimens are injection molded from these test formulations.

The specimens are tested for flame retardancy according to the UL-94 burn test specifications. The molded specimens containing the hindered amine compounds exhibit flame retardancy.

EXAMPLE 48

Molding grade polystyrene is dry-blended with test additives and then melt compounded. In addition to the hindered amines, selected flame retardants are also included in the test formulations. Specimens are injection molded from these test formulations.

The specimens are tested for flame retardancy according to the UL-94 burn test specifications. The molded specimens containing the hindered amine compounds and selected flame retardants exhibit flame retardancy.

EXAMPLE 49

Foam grade polystyrene is dry-blended with hindered amine test additives and then melt compounded. Foam polystyrene specimens are prepared from these test formulations.

The specimens are tested for flame retardancy according to the UL-94 bum test specifications. The foam specimens containing the hindered amine compounds exhibit flame retardancy.

EXAMPLE 50

Foam grade polystyrene is dry-blended with test additives and then melt compounded. In addition to the hindered amines, selected flame retardants are also included in these test formulation. Foam polystyrene specimens are prepared from these test formulations.

The specimens are tested for flame retardancy according to the UL-94 bum test specifications. The foam specimens containing the hindered amine compounds and flame retardants exhibit flame retardancy.

What is claimed is:

1. A flame retardant polymer composition which comprises
(a) a polymer substrate, and
(b) an effective flame retarding amount of a synergistic mixture of
   (i) a hindered amine and
   (ii) a brominated flame retardant;
      wherein said composition comprises essentially no antimony oxides,
      wherein the hindered amine of component (i) is selected from the group consisting of (A), (B) and (IIIb),
      wherein
      (A) is $$\left[\begin{array}{c} RCH_2 \underset{RCH_2}{\overset{CH_3}{\diagup}} \underset{CH_3}{\overset{R}{\diagdown}} \\ E-N \underset{}{\diagdown} \underset{}{\diagup} O-R_2 \end{array}\right]_m$$

wherein
E is alkoxy of 1 to 18 carbon atoms, cycloalkoxy of 5 to 12 carbon atoms or aralkoxy of 7 to 15 carbon atoms, or E is —O—T—(OH)$_b$,
T is a straight or branched chain alkylene of 1 to 18 carbon atoms, cycloalkylene of 5 to 18 carbon atoms, cycloalkenylene of 5 to 18 carbon atoms, a straight or branched chain alkylene of 1 to 4 carbon atoms substituted by phenyl or by phenyl substituted by one or two alkyl groups of 1 to 4 carbon atoms;
b is 1, 2 or 3 with the proviso that b cannot exceed the number of carbon atoms in T, and when b is 2 or 3, each hydroxyl group is attached to a different carbon atoms of T;
R is hydrogen or methyl,
m is 1 to 4,
when m is 1,
$R_2$ is hydrogen, $C_1$–$C_{18}$alkyl or said alkyl optionally interrupted by one or more oxygen atoms, $C_2$–$C_{12}$alkenyl, $C_6$–$C_{10}$aryl, $C_7$–$C_{18}$aralkyl, glycidyl, a monovalent acyl radical of an aliphatic, cycloaliphatic or aromatic carboxylic acid, or a carbamic acid, or

[structure: bis-phenol benzoate with C(CH_3)_3 substituents, HO—Ar—C(=O)—O—Ar—C(=O)—, subscript x]

wherein x is 0 or 1, or

[structure: piperidine with CH_3 groups, (CH_2)_y N-lactam, N—CH_2—C(=O)—]

wherein y is 2–4;
when m is 2,
$R_2$ is $C_1$–$C_{12}$alkylene, $C_4$–$C_{12}$alkenylene, xylylene, a divalent acyl radical of an aliphatic, cycloaliphatic, araliphatic or aromatic dicarboxylic acid or of a dicarbamic acid, or

[structures showing D_1, D_2, C branching with C=O groups; or D_3—CH—C(=O)—, CH_2—C(=O)]

—C(=O)—NH—(CH_2)_d—NH—C(=O)— wherein $D_1$ and $D_2$ are independently hydrogen, an alkyl radical containing up to 8 carbon atoms, an aryl or aralkyl radical including 3,5-di-t-butyl-4-hydroxybenzyl radical, $D_3$ is hydrogen, or an alkyl or alkenyl radical containing up to 18 carbon atoms, and d is 0–20;
when m is 3, $R_2$ is a trivalent acyl radical of an aliphatic, unsaturated aliphatic, cycloaliphatic, or aromatic tricarboxylic acid;
when m is 4, $R_2$ is a tetravalent acyl radical of a saturated or unsaturated aliphatic or aromatic tetracarboxylic acid including 1,2,3,4-butanetetracarboxylic acid, 1,2,3,4-but-2-enetetracarboxylic, and 1,2,3,5- and 1,2,4,5-pentanetetracarboxylic acid;
wherein
(B) is a mixture of N,N',N'''-tris{2,4-bis[(1-hydrocarbyloxy-2,2,6,6-tetramethylpiperidin-4- yl)alkylamino]-s-triazin-6-yl}-3,3'-ethylenediiminodipropylamine; N,N',N"-tris{2,4-bis[(1-hydrocarbyloxy-2,2,6,6-tetramethylpiperidin-4-yl)alkylamino]-s-triazin-6-yl}-3,3'-ethylenediiminodipropylamine IIA, and bridged derivatives as described by formulas I, II, and III $R_1NH$—$CH_2CH_2CH_2NR_2CH_2CH_2NR_3CH_2CH_2CH_2NHR_4$ (I)
T—$E_1$—$T_1$ (II)
T—$E_1$ (IIA)
G—$E_1$—$G_1$—$E_1$—$G_2$ (III)

where in the tetraamine of formula I
$R_1$ and $R_2$ are the s-triazine moiety E; and one of $R_3$ and $R_4$ is the s-triazine moiety E with the other of $R_3$ or $R_4$ being hydrogen,
E is

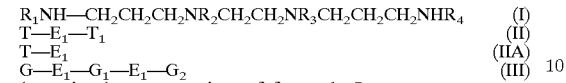

R is methyl, propyl, cyclohexyl or octyl,
$R_5$ is alkyl of 1 to 12 carbon atoms,
where in the compound of formula II or IIA when R is propyl, cyclohexyl or octyl,
T and $T_1$ are each a substituted by $R_1$–$R_4$ as is defined for formula I, where
(1) one of the s-triazine moieties E in each tetraamine is replaced by the group $E_1$ which forms a bridge between two tetraamines T and $T_1$,
$E_1$ is

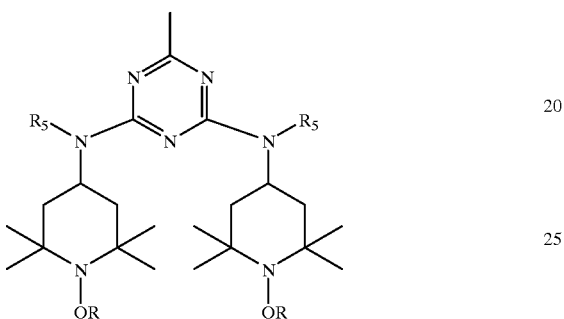

or
(2) the group $E_1$ can have both termini in the same tetraamine T as in formula IIA where two of the E moieties of the tetraamine are replaced by one $E_1$ group, or
(3) all three s-triazine substituents of tetraamine T can be $E_1$ such that one $E_1$ links T and $T_1$ and a second $E_1$ has both termini in tetraamine T,
L is propanediyl, cyclohexanediyl or octanediyl;
where in the compound of formula III
G, $G_1$ and $G_2$ are each tetraamines substituted by $R_1$–$R_4$ as defined for formula I, except that G and $G_2$ each have one of the s-triazine moieties E replaced by $E_1$, and $G_1$ has two of the triazine moieties E replaced by $E_1$, so that there is a bridge between G and $G_1$ and a second bridge between $G_1$ and $G_2$;

which mixture is prepared by reacting two to four equivalents of 2,4-bis[(1-hydrocarbyloxy-2,2,6,6-piperidin-4-yl)butylamino]-6-chloro-s-triazine with one equivalent of N,N'-bis(3-aminopropyl)-ethylenediamine; and
wherein
(IIIb) is

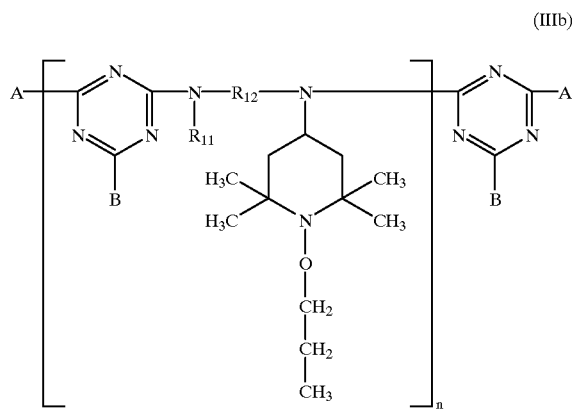

in which the index n ranges from 1 to 15;
$R_{12}$ is $C_2$–$C_{12}$alkylene, $C_4$–$C_{12}$alkenylene, $C_5$–$C_7$cycloalkylene, $C_5$–$C_7$cycloalkylene-di($C_1$–$C_4$alkylene), $C_1$–$C_4$alkylenedi($C_5$–$C_7$cycloalkylene), phenylenedi($C_1$–$C_4$alkylene) or $C_4$–$C_{12}$alkylene interrupted by 1,4-piperazinediyl, —O— or >N—$X_1$ with $X_1$ being $C_1$–$C_{12}$acyl or ($C_1$–$C_{12}$alkoxy)carbonyl or having one of the definitions of $R_{14}$ given below except hydrogen; or $R_{12}$ is a group of the formula (Ib') or (Ic');

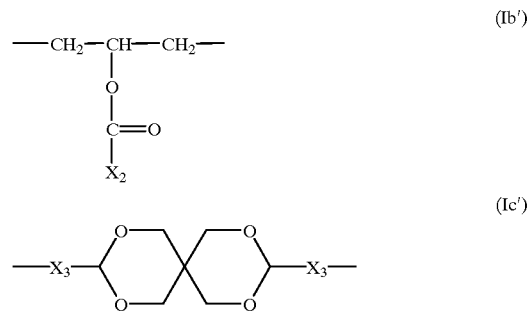

with m being 2 or 3,
$X_2$ being $C_1$–$C_{18}$alkyl, $C_5$–$C_{12}$cycloalkyl which is unsubstituted or substituted by 1, 2 or 3 $C_1$–$C_4$alkyl; phenyl which is unsubstituted or substituted by 1, 2 or 3 $C_1$–$C_4$alkyl or $C_1$–$C_4$alkoxy; $C_7$–$C_9$phenylalkyl which is unsubstituted or substituted on the phenyl by 1, 2 or 3 $C_1$–$C_4$alkyl; and the radicals $X_3$ being independently of one another $C_2$–$C_{12}$alkylene;
$R_{13}$, $R_{14}$ and $R_{15}$, which are identical or different, are hydrogen, $C_1$–$C_{18}$alkyl, $C_5$–$C_{12}$cycloalkyl which is unsubstituted or substituted by 1, 2 or 3 $C_1$–$C_4$alkyl; $C_3$–$C_{18}$alkenyl, phenyl which is unsubstituted or substituted by 1, 2 or 3 $C_1$–$C_4$alkyl or $C_1$–$C_4$alkoxy; $C_7$–$C_9$phenylalkyl which is unsubstituted or substituted on the phenyl by 1, 2 or 3 $C_1$–$C_4$alkyl; tetrahydrofurfuryl or $C_2$–$C_4$alkyl which is substituted in the 2, 3 or 4 position by —OH, $C_1$–$C_8$alkoxy, di($C_1$–$C_4$alkyl)amino or a group of the formula (Ie');

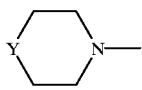

with Y being —O—, —CH$_2$—, —CH$_2$CH$_2$— or >N—CH$_3$, or —N(R$_{14}$(R$_{15}$) is additionally a group of the formula (Ie');

the radicals A are independently of one another —OR$_{13}$, —N(R$_{14}$(R$_{15}$) or a group of the formula (IIId);

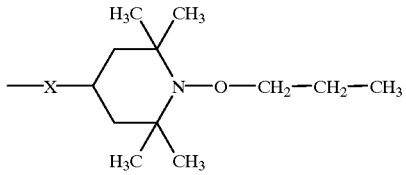

X is —O— or >N—R$_{16}$;

R$_{16}$ is hydrogen, C$_1$–C$_{18}$alkyl, C$_3$–C$_{18}$alkenyl, C$_5$–C$_{12}$cycloalkyl which is unsubstituted or substituted by 1, 2 or 3 C$_1$–C$_4$alkyl; C$_7$–C$_9$phenylalkyl which is unsubstituted or substituted on the phenyl by 1, 2 or 3 C$_1$–C$_4$alkyl; tetrahydrofurfuryl, a group of the formula (IIIf),

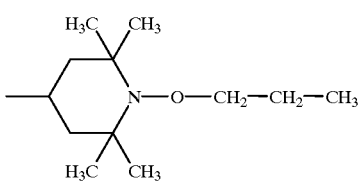

or C$_2$–C$_4$alkyl which is substituted in the 2, 3 or 4 position by —OH, C$_1$–C$_8$alkoxy, di(C$_1$–C$_4$alkyl) amino or a group of the formula (Ie');

R$_{11}$ has one of the definitions given for R$_{16}$; and the radicals B have independently of one another one of the definitions given for A;

with the proviso that when the polymer substrate is polypropylene, the flame retardant is not a halogenated hydrocarbyl phosphate or phosphonate.

2. A composition according to claim 1 wherein the polymer substrate is selected from the group of resins consisting of the polyolefins, the thermoplastic olefins, styrenic polymers and copolymers, and ABS.

3. A composition according to claim 2 wherein the polymer substrate is polypropylene, polyethylene, thermoplastic olefin (TPO), ABS and high impact polystyrene.

4. A composition according to claim 3 wherein the polymer substrate is polypropylene, polyethylene or thermoplastic olefin (TPO).

5. A composition according to claim 1 wherein the effective flame retarding amount of a hindered amine of component (i) is 0.05 to 10% by weight based on the polymer substrate.

6. A composition according to claim 5 wherein the effective flame retarding amount of a hindered amine of component (i) is 0.5 to 8% by weight based on the polymer substrate.

7. A composition according to claim 6 wherein the effective flame retarding amount of a hindered amine of component (i) is 0.5 to 2% by weight based on the polymer substrate.

8. A composition according to claim 1 where in the hindered amine of formula A of component (i) E is alkoxy of 1 to 18 carbon atoms, cycloalkoxy of 5 to 12 carbon atoms or aralkoxy of 7 to 15 carbon atoms.

9. A composition according to claim 8 wherein E is methoxy, propoxy, cyclohexyloxy or octyloxy.

10. A composition according to claim 9 wherein E is propoxy, cyclohexyloxy or octyloxy.

11. A composition according to claim 10 wherein E is cyclohexyloxy.

12. A composition according to claim 1 wherein the effective flame retarding amount of the synergistic mixture of component (b) is 0.5 to 30% by weight based on component (a).

13. A composition according to claim 1 wherein the flame retardant component (ii) is selected from the group consisting of polybrominated diphenyl oxide (DE-60F)
decabromodiphenyl oxide (DBDOP),
bis(2,3-dibromopropyl ether) of bisphenol A (PE68),
brominated epoxy resin,
ethylene-bis(tetrabromophthalimide) (BT93),
1,2-bis(tribromophenoxy)ethane (FF680), and
tetrabromo-bisphenol A (SAYTEX® RB100).

14. A composition according to claim 13 wherein the flame retardant compound (ii) decabromodiphenyl oxide.

15. A composition according to claim 1 wherein further comprising a coadditive which is a phosphorus compound selected from the group consisting of tris(2,4-di-tert-butylphenyl) phosphite, bis(2,4-di-tert-butyl-6-methylphenyl) ethyl phosphite, 2,2',2"-nitrilo[triethyl-tris-(3,3',5,5'-tetra-tert-butyl-1,1'-biphenyl-2,2'-diyl) phosphite], tetrakis(2,4-di-butylphenyl) 4,4'-biphenylenediphosphonite, tris(nonylphenyl) phosphite, bis(2,4-di-tert-butylphenyl) pentaerythrityl diphosphite, 2,2'-ethylidenebis(2,4-di-tert-butylphenyl) fluorophosphite and 2-butyl-2-ethylpropan-1,3-diyl 2,4,6-tri-tert-butylphenyl phosphite; or a UV absorber selected from the group consisting of 2-(2-hydroxy-3,5-di-α-cumylphenyl)-2H-benzotriazole, 2-(2-hydroxy-5-methylphenyl)-2H-benzotriazole, 5-chloro-2-(2-hydroxy-3,5-di-tert-butylphenyl)-2H-benzotriazole, 2-(2-hydroxy-3,5-di-tert-amylphenyl)-2H-benzotriazole, 2-(2-hydroxy-3-α-cumyl-5-tert-octylphenyl)-2H-benzotriazole, 2,4-di-tert-butylphenyl 3,5-di-tert-butyl4-hydroxybenzoate, 2-hydroxy-4-n-octyloxybenzophenone and 2,4-bis(2,4-dimethy-phenyl)-6-(2-hydroxy-4-octyloxyphenyl)-s-triazine.

16. A composition according to claim 1 wherein the hindered amine of component (i) is (a) the mixture of compounds of formula I, II, IIA and III where R is cyclohexyl;

(b) 1-cyclohexyloxy-2,2,6,6-tetramethyl-4-octadecylaminopiperidine;

(c) bis(1-octyloxy-2,2,6,6-tetramethylpiperidin-4-yl) sebacate;

(d) 2,4-bis[(1-cyclohexyloxy-2,2,6,6-tetramethylpiperidin-4-yl)butylamino]-6-(2-hydroxyethylamino-s-triazine;

(e) bis(1-cyclohexyloxy-2,2,6,6-tetramethylpiperidin-4-yl) adipate;

(f) the oligomeric compound which is the condensation product of 4,4'-hexamethylene-bis(amino-2,2,6,6-tetramethylpiperidine) and 2,4-dichloro-6-[(1-octyloxy-2,2,6,6-tetramethylpiperidin-4-yl)butylamino]-s-triazine end-capped with 2-chloro-4,6-bis(dibutylamino)-S-triazine;

(g) the oligomeric compound which is the condensation product of 4,4'-hexamethylene-bis(amino-2,2,6,6-tetramethylpiperidine) and 2,4-dichloro-6-[(1-cyclohexyloxy-2,2,6,6-tetramethylpiperidin-4-yl)butylamino]-s-triazine end-capped with 2-chloro-4,6-bis(dibutylamino)-S-triazine;

(h) 2,4-bis[(1-cyclohexyloxy-2,2,6,6-piperidin-4-yl)butylamino]-6-chloro-s-triazine;

(i) 1-(2-hydroxy-2-methylpropoxy)-4-octadecanoyloxy-2,2,6,6-tetramethylpiperidine or (j) the compound of formula

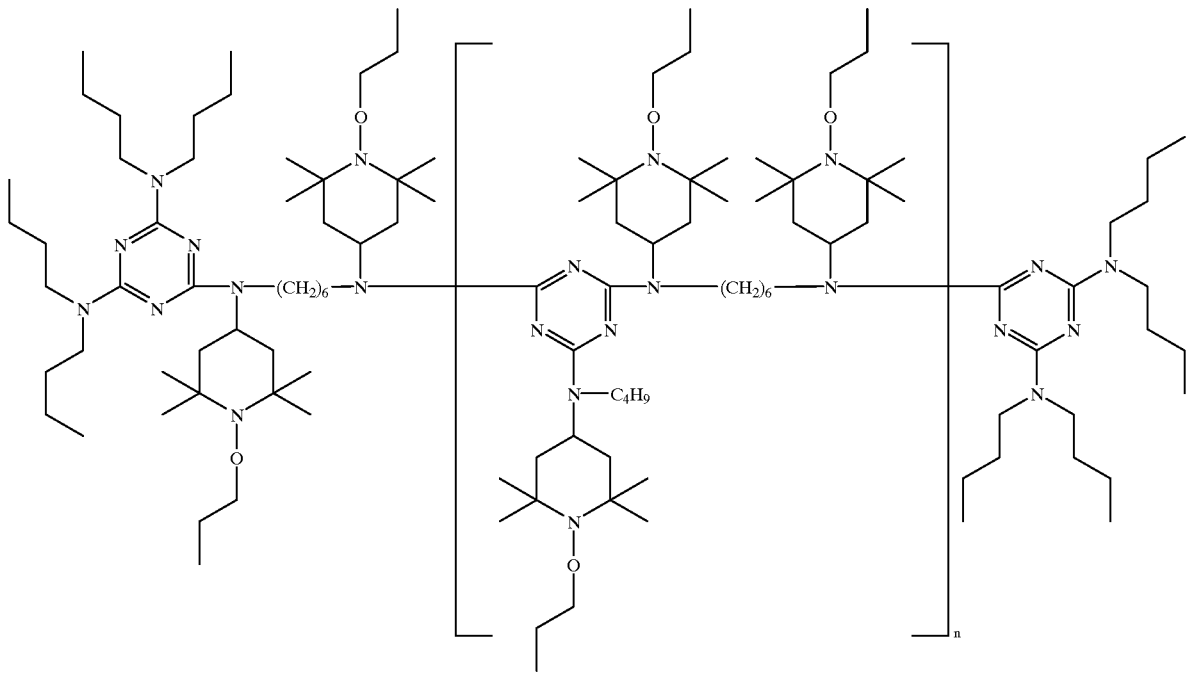
17. A composition according to claim 16 wherein the hindered amine of component (i) is
   (a) the mixture of compounds of formula I, II, IIA and III where R is cyclohexyl;
   (c) bis(1-octyloxy-2,2,6,6-tetramethylpiperidin-4-yl) sebacate;
   (i) 1-(2-hydroxy-2-methylpropoxy)-4-octadecanoyloxy-2,2,6,6-tetramethylpiperidine; or
   (j) the compound of formula
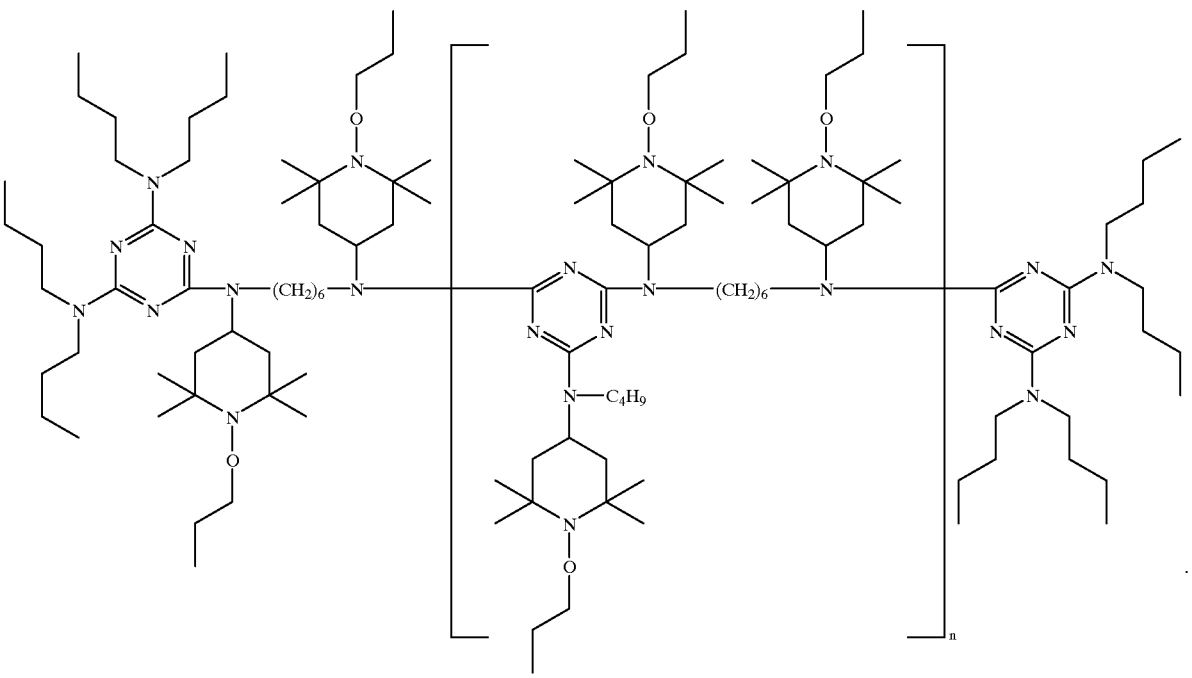
* * * * *